(12) United States Patent
Suddaby

(10) Patent No.: US 11,213,402 B2
(45) Date of Patent: Jan. 4, 2022

(54) ENDOSCOPICALLY IMPLANTABLE INFLATABLE INTERBODY FUSION DEVICE

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 538 days.

(21) Appl. No.: 15/403,544

(22) Filed: Jan. 11, 2017

(65) Prior Publication Data

US 2018/0193158 A1  Jul. 12, 2018

(51) Int. Cl.
| | |
|---|---|
| *A61F 2/44* | (2006.01) |
| *A61F 2/46* | (2006.01) |
| *A61F 2/30* | (2006.01) |
| *A61F 2/28* | (2006.01) |

(52) U.S. Cl.
CPC ............ *A61F 2/441* (2013.01); *A61F 2/4455* (2013.01); *A61F 2/4611* (2013.01); *A61F 2002/2817* (2013.01); *A61F 2002/3008* (2013.01); *A61F 2002/30583* (2013.01); *A61F 2002/30586* (2013.01); *A61F 2002/30841* (2013.01)

(58) Field of Classification Search
CPC .................................. A61F 2/44; A61F 2/441
USPC ............................................ 623/17.11–17.16
See application file for complete search history.

(56) References Cited

U.S. PATENT DOCUMENTS

| | | | |
|---|---|---|---|
| 3,867,728 A * | 2/1975 | Stubstad | A61F 2/30907 623/17.16 |
| 4,932,969 A * | 6/1990 | Frey | A61F 2/441 623/17.12 |
| 5,123,926 A * | 6/1992 | Pisharodi | A61F 2/441 606/247 |
| 5,505,732 A | 4/1996 | Michelson | |
| 5,674,295 A | 10/1997 | Ray et al. | |
| 6,007,483 A | 12/1999 | Kieturakis | |
| 6,332,894 B1 * | 12/2001 | Stalcup | A61B 17/7097 623/17.11 |
| 6,395,034 B1 | 5/2002 | Suddaby | |
| 6,706,069 B2 | 3/2004 | Berger | |
| 6,837,850 B2 | 1/2005 | Suddaby | |
| 6,958,077 B2 | 10/2005 | Suddaby | |
| 6,969,405 B2 | 11/2005 | Suddaby | |
| 7,128,746 B2 | 10/2006 | Singer et al. | |
| 7,220,282 B2 | 5/2007 | Kuslich | |
| 7,597,714 B2 | 10/2009 | Suddaby | |
| 7,749,270 B2 | 7/2010 | Peterman | |
| 7,758,649 B2 | 7/2010 | Walsh et al. | |
| 7,776,073 B2 | 8/2010 | Serhan et al. | |
| 8,292,961 B2 | 10/2012 | Osman | |

(Continued)

OTHER PUBLICATIONS www.K2M.com, Sahara, AL Expandable Stabilization System, Leesburg, Virginia 20175 USA, last accessed Feb. 7, 2017.

*Primary Examiner* — Si Ming Ku
(74) *Attorney, Agent, or Firm* — Simpson & Simpson, PLLC; Michael Nicholas Vranjes

(57) ABSTRACT

An endoscopically implantable inflatable interbody fusion device, including an inflatable body having a first inner wall and an outer wall, a first cavity defined by the first inner wall, at least one hollow space between the first inner wall and the outer wall, a first delivery tube extending from outside the outer wall into the at least one hollow space, and a second delivery tube extending from outside the outer wall, through the at least one hollow space, and terminating in the first cavity.

22 Claims, 19 Drawing Sheets

(56) References Cited

U.S. PATENT DOCUMENTS

| | | |
|---|---|---|
| 8,632,592 B2 | 1/2014 | Barrall |
| 8,734,459 B1 | 5/2014 | Alobaid |
| 8,758,407 B2 | 6/2014 | Protopsaltis et al. |
| 9,023,048 B2 | 5/2015 | Osman |
| 9,186,259 B2 | 11/2015 | To et al. |
| 2002/0173851 A1 | 11/2002 | McKay |
| 2007/0276491 A1 | 11/2007 | Ahrens et al. |
| 2007/0299523 A1 | 12/2007 | Pflum |
| 2008/0033575 A1 | 2/2008 | Walsh et al. |
| 2008/0154305 A1 | 6/2008 | Foley et al. |
| 2008/0154373 A1 | 6/2008 | Protopsaltis et al. |
| 2009/0012618 A1 | 1/2009 | Ahrens et al. |
| 2009/0138015 A1* | 5/2009 | Conner ............... A61B 17/1615 606/80 |
| 2009/0171389 A1 | 7/2009 | Sankaran |
| 2009/0171390 A1 | 7/2009 | Sankaran |
| 2009/0312837 A1 | 12/2009 | Eisermann et al. |
| 2010/0070041 A1 | 3/2010 | Peterman et al. |
| 2010/0234952 A1 | 9/2010 | Peterman |
| 2010/0256766 A1* | 10/2010 | Hibri ....................... A61F 2/441 623/17.16 |
| 2010/0331983 A1 | 12/2010 | Sankaran |
| 2011/0004307 A1* | 1/2011 | Ahn ....................... A61F 2/441 623/17.12 |
| 2011/0190895 A1 | 8/2011 | Segal et al. |
| 2011/0202135 A1 | 8/2011 | Baek et al. |
| 2012/0310352 A1 | 12/2012 | DiMauro et al. |
| 2013/0090734 A1 | 4/2013 | Pflum |
| 2013/0165975 A1 | 6/2013 | Tebbe et al. |
| 2014/0303730 A1 | 10/2014 | McGuire et al. |
| 2014/0379086 A1 | 12/2014 | Elahinia et al. |
| 2016/0310286 A1* | 10/2016 | McJunkin ............... A61F 2/441 |

* cited by examiner

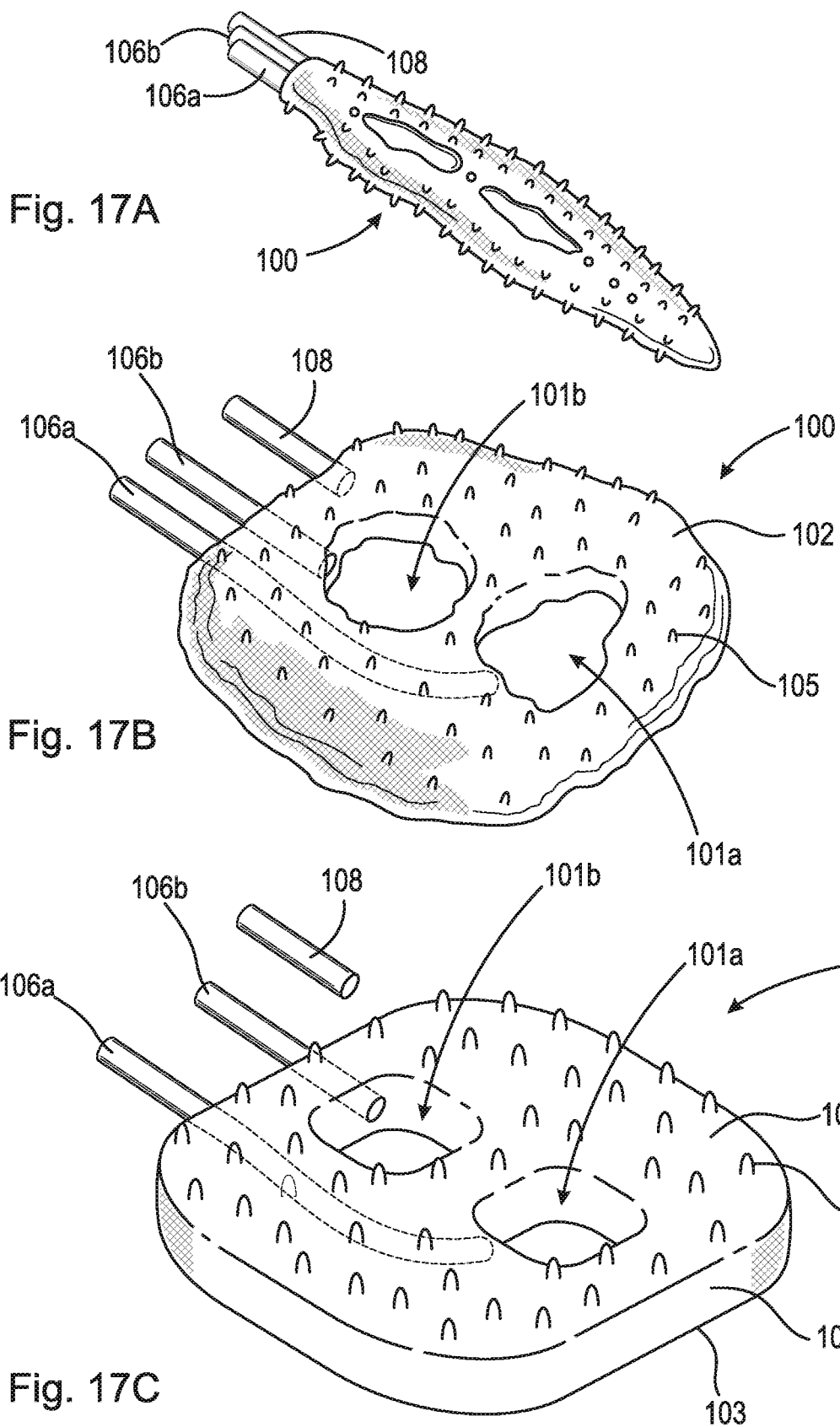

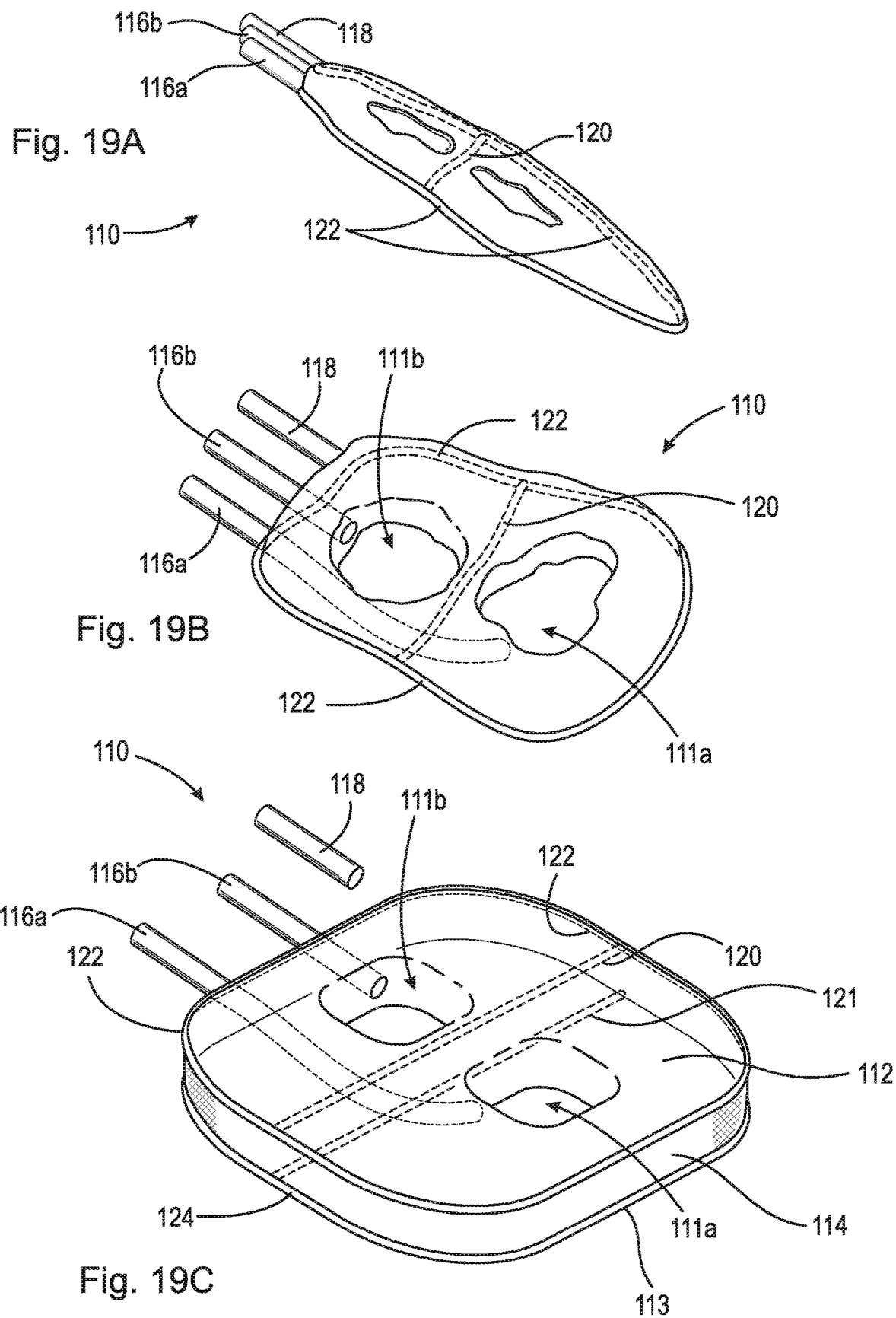

ENDOSCOPICALLY IMPLANTABLE INFLATABLE INTERBODY FUSION DEVICE

FIELD

The present disclosure relates to orthopedic surgery, and more particularly to a prosthetic interbody fusion device to replace a damaged intervertebral disc and a surgical procedure for implanting the construct in the intervertebral disc space.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

One common tool used in these spinal surgical procedures is an endoscope. A representative endoscope 30 is shown in FIG. 7A. Endoscopes are complex biomedical devices. The complexity results from the need for fiberoptic bundles and multiple long narrow channels to be contained within a tubular structure that is constrained by the limited dimensions of the body cavity opening. As shown in FIG. 7A, endoscope 30 broadly comprises light guide connector 31, light guide tube 32, control body 33, and insertion tube 34. As will be described infra, the inflatable abrading device of the embodiment is introduced into the disc space via insertion tube 34. As shown in FIG. 7B, surgeon 40 uses the endoscope both to observe and guide the procedure via monitor 41, and to introduce and manipulate surgical instruments and tools during surgery on patient 45.

The endoscope is only one element of the system. Other required elements are a light source, video processor, monitor and water bottle. For the purpose of describing an endoscope in this disclosure, we refer to videoscopes, which represent a newer technology in endoscope development as compared to fiberoptic endoscopes. In videoscopes, the "viewing" fibre bundle is replaced by a miniature charged coupled device (CCD) video camera chip that transmits signals via wires.

Videoscopes include three major sections: connector 31 (sometimes referred to as the "umbilical" section), control body 33 and insertion tube 34. Endoscopes require a watertight internal compartment integrated through all components for electrical wiring and controls, which protects them from exposure to patient secretions during use and facilitates the endoscope being submerged for cleaning and subsequent disinfection. Example embodiments are not intended to be limited to any particular type of endoscope.

Control body 33 provides connections for four systems: the electrical system, the light system, the air and water system, and the suction system. A cable with video signal, light control, and remote switching from the video processor is connected in the electrical system. A watertight cap is required for leak testing and reprocessing. The electrical connector is the only opening to the internal components. The connector is inserted into the light source and directs light via the fiberoptic bundle in the light guide to the distal end of the insertion tube. Air pressure is provided from a pump to the air pipe, and the water bottle is also connected here (there is no water channel or water connection for bronchoscopes). In some endoscope models, the separate air and water channels merge just prior to the distal end where they exit through a single channel. In other models, the air and water channels are totally separate and do not merge. The air and water channels are usually of one millimeter internal diameter, which is too small for brushing. A portable or wall suction system is connected to the suction port. The Universal cord encases the electrical wiring and air, water and suction channels from the connector to the control section. Teflon® (PTFE) tubing is commonly used for channels, and advances in technology have led to more pliable and smooth materials for instrument channels with better anti-adhesion properties. The suction channel size can vary from two to four millimeters internal diameter depending on scope make and model. There is a biopsy port on the side of the insertion tube that allows instruments to be passed down the insertion tube to the distal end (referred to as the instrument channel or biopsy/suction channel).

Control body 33 has moveable knobs that allow the physician to control all scope functions. The angulation control knobs drive the angulation wires and control the bending section at the distal end of the insertion tube, thereby providing two-dimensional angulation. Locking mechanisms are provided to hold the bending section in a specific position. The suction cylinder and valve connects the suction channel to the instrument channel in the insertion tube. By pressing the valve button, suction can be provided to the instrument channel. The air/water cylinder and valve are similar to the suction cylinder/valve except that a two-way button valve is used in a dual channel cylinder thereby providing air or water to the lens at the distal end to wash and insufflate for better vision. Both valves are removable for cleaning. The air and water channels also require a cleaning adapter valve that is to be used at the end of each procedure. Insertion of the cleaning adapter initiates air flow through both air and water channels, and once activated, water is pumped through both channels. The instrument channel port (often referred to as the "biopsy port") is located on the lower part of the control section. It enters the instrument channel at a Y-piece union with the suction channel. A valve is required to close the port so that suctioning may be facilitated. Remote switches present on the top of the control section are usually programmable, allowing control of the video processor (i.e., contrast, iris and image capture functions).

The normal intervertebral disc has an outer fibrous ring, constituted mainly of collagen fibers, which strongly binds the vertebral elements together. This fibrous outer layer, or annulus, encircles a soft gel-like matrix, or nucleus, which serves both as a cushion and as a mobile and compressible element that allows motion to occur between the vertebral bodies above and below the intervertebral disc. This gel matrix is 95% water. The types of motion that can occur at the level of the intervertebral disc include flexion, extension, lateral bending, and varying degrees of torsion or rotation.

In the course of a day, the normal intervertebral disc may encounter various combinations of these bending or twisting motions several thousand times. As a consequence of such repetitive motion, natural discs deteriorate over time, much as the padded cushion on a well-used chair might do. The effect of this deterioration is a loss of water content of the gel matrix of the nucleus and a concomitant compacting of its fibers with a resultant loss of disc space height, which in turn causes a slackening or laxity of the surrounding support ligaments of the spine and the development of what is termed degenerative instability. This instability results in a pathologic excess of movement at the intervertebral disc space that further accentuates the degeneration of both the nucleus and the annulus of the disc, as well as the posterior facet joints and associated ligaments. With continued deterioration, the annulus of the disc can bulge or even develop radial tears that allow the inner nucleus material to protrude or even extrude from the disc space. This bulging of the annulus or protrusion of the nucleus can compress nerves and cause disabling sciatic pain. Distension or bulging of the annulus alone is frequently sufficient to produce disabling back pain because of compression or inflammation of free nerve endings (pain fibers) present in the outer annulus of the disc.

The time-honored method of addressing degenerative lumbar instability resulting from severely damaged intervertebral discs has been to remove the damaged disc completely and fuse together the two adjacent vertebral bones to eliminate pathological motion.

While initial interbody fusions were performed simply by inserting blocks of allograft or autograft bone, it soon became clear that procedures involving the insertion of structural bone grafts into the disc space alone were fraught with complications, most commonly related to graft expulsion or graft structural failure.

To mitigate these problems, cylindrical threaded interbody fusion devices or implants have been developed as in, inter alia, U.S. Pat. No. 5,505,732 (Michelson) and U.S. Pat. No. 5,674,295 (Ray et al.), to hold allograft or autograft bone in position, thereby protecting the graft from expulsion or crushing while bony fusion took place. These devices worked well for protecting bone graft and fostering fusion, but required a large surgical incision to implant them as well as substantial manipulation of either nerves or blood vessels to properly situate and anchor them within the disc space.

Later versions of theses cages were made of PEEK (polyetheretherketone) for purported radiolucent advantages and to allow for use of non-cylindrical shapes which permitted height versus width changes that cylindrical devices could not provide.

More recently, expandable PEEK and titanium cages have been developed to permit minimally invasive approaches.

Clearly the evolution of interbody fusion devices has been toward smaller incisions and lesser degrees of neurovascular manipulation for obvious advantages. Reduced tissue disruption from the surgical procedure itself means fewer complications, less pain, faster return to normal activity, shorter hospital stays, and minimized scar tissue formulation once healing occurs.

At present, the least invasive surgeries are generally accomplished through an endoscope which allows surgical access through incisions measured in millimeters rather than the centimeters needed for most so-called minimally invasive surgeries.

Clearly, there is a need in the art and science of spinal fusion surgery for an interbody fusion device, which can be administered and practiced entirely through an endoscope such that true minimally invasive surgeries can be performed.

SUMMARY

According to aspects illustrated herein, there is provided an endoscopically implantable inflatable interbody fusion device, comprising an inflatable body having a first inner wall and an outer wall, a first cavity defined by the first inner wall, at least one hollow space between the first inner wall and the outer wall, a first delivery tube extending from outside the outer wall into the at least one hollow space, and a second delivery tube extending from outside the outer wall, through the at least one hollow space, and terminating in the first cavity.

According to aspects illustrated herein, there is provided an endoscopically implantable inflatable interbody fusion device, comprising an inflatable body, including a first inner wall, a second inner wall, and an outer wall, a first cavity defined by the first inner wall, a second cavity defined by the second inner wall, at least one hollow space between the first and second inner walls and the outer wall, a first delivery tube extending from outside the outer wall into the at least one hollow space, a second delivery tube extending from outside the outer wall, through the at least one hollow space, and terminating in the first cavity, and a third delivery tube extending from outside the outer wall, through the at least one hollow space, and terminating in the second cavity.

According to aspects illustrated herein, there is provided an endoscopically implantable inflatable interbody fusion device, comprising a first inflatable body, including a first inner wall, a first outer wall, and a first hollow space between the first inner and outer wall, a second inflatable body removably connected to the first inflatable body, including a second inner wall, a second outer wall, and a second hollow space between the second inner and outer wall, a first cavity defined by the first and second inner walls, a first delivery tube extending from outside the first outer wall into the first hollow space, a second delivery tube extending from outside the second outer wall into the second hollow space, and a third delivery tube extending from outside the first outer wall, through the first hollow space, and terminating in the first cavity.

One embodiment relates to a spinal interbody fusion implant capable of being deployed through the working channel of an endoscope, and constructed in situ such that the form and function of any interbody device presently in use can be practiced through incisions many times smaller than the device being implanted.

The preferred embodiment comprises one or more inflatable chambers capable of being insufflated with a hardenable material via a connecting tube or tubes which can be detached from the chamber once the chamber is inflated to the appropriate dimensions.

The chamber (or chambers) is/are first inflated with radiopaque contrast material under fluoroscopic visualization to ensure that chamber inflation and the device geometry or shape results in a restoration of disc space height thereby ensuring that the final inflated size of the chamber is sufficient to stabilize the disc segment being replaced. The volume of contrast necessary to achieve proper size and shape is recorded and an identical amount of hardenable material is prepared for instillation.

The contrast material is then aspirated and replaced with an equivalent volume of hardenable material, which is injected into the chamber and allowed to solidify. Once solid, the inflated chamber defines a particular geometric shape and intervening space between them into which biologics or bone products can be placed to facilitate fusion. In effect, an interbody fusion implant or prosthesis is constructed or formulated within the interbody space, through the smallest possible opening, by virtue of the distensible nature of the device, and its ability to assume any of a number of forms or shapes.

Because of its deformable and distensible nature, the inflatable chamber conforms to the structural variations in a vertebral body endplate allowing for a completely customized endoprosthesis in every case. This intimate contact between the device and the endplate substantially increases the contact surface area and thereby enhances immediate stability and reduces the risk of device subsidence, or device migration.

The chamber walls may be coated with material that favors bony ingrowth, for example hydroxyapatite, or alternatively be made of material that completely resorbs overtime, such as polyglycolic acid or polylactic acid. The walls may also contain metal studs to serve as radiographic markers and to aid in preventing dislodgement. The walls may contain perimeter or crossing cables made of metal to bolster structural strength and/or to serve as radiographic markers.

Suitable nonabsorbable materials for the chamber walls include, but are not limited to, a Kevlar® material, plastic or polypropylene, carbon fiber mesh, and/or PEEK mesh. Suitable absorbable materials for the chamber walls include, but are not limited to, polyglycolic, polylactic acid, polycaprolactone, and polydioxanone. Suitable injectable hardenable material include, but are not limited to, a variety of biocompatible resins or polymers such as PMMA, polycarbonate resins, epoxy resins, polyamide resins, and poly (methyl methacrylate).

The inflatable chamber walls expand in an elastomeric fashion or in a non-elastomeric fashion, depending on surgical need, surgical pathology, or surgeon preference.

In an elastomeric version, the chamber walls expand in a fashion akin to a latex balloon. In this iteration, the chamber expands in multiple directions as it enlarges to its final shape. Vertical expansion is limited by the adjacent endplate, lateral expansion by the disc annulus, and medial expansion by inserted bony graft material or biologics. In this iteration there may be an advantage in insertion of bony graft material and/or biologics into the center cavity defined by the chamber, as inflation of the chamber pushes in on the graft material thereby forcing it against the endplates, and favoring fusion by Wolff's law.

The elastomeric surface conforms to surrounding anatomy as it is displaced outwardly by hydraulic forces allowing it to conform to the shape of the surrounding tissues it encounters, and thereby forms a perfectly customized endoprosthesis once hardenable material is injected and allowed to set.

If desired, the elastomeric chamber could be removed by puncturing its wall, in a fashion akin to puncturing an elastomeric balloon filled with water which has been frozen. In this embodiment, the elastomeric chamber serves merely as a formulation or implantation device and can be entirely removed leaving the hardened material as the sole interbody construct.

The chamber is filled by a connecting tube. The tube is preferably flexible and nondistensible. The tube fits down the working channel of the endoscope and is detachable from the inflated chamber once the injected material has hardened.

In the non-elastomeric version, the chamber walls are made of material that is not distensible (or minimally distensible) such that a relatively nonconforming final shape is achieved. Unlike the elastomeric version, which expands like a latex balloon, this version expands to a predetermined shape and size, much like an inflatable raft, inflatable pool, or inflatable boat.

In this iteration, the chamber walls are largely non-elastomeric and form a predetermined shape and size when fully inflated with a hardenable material. The chamber walls may be covered in material, such as hydroxyapatite, to permit tissue ingrowth from adjacent vertebral body endplates. The chamber walls may contain studs which engage the endplate and resist expulsion. The chamber walls may be made of an absorbable material, such as polyglycolic acid or polylactic acid, which completely absorb over time leaving the hardenable material in place after they have been resorbed. In essence, the absorbable iteration acts like a cement form in a building which is removed once the cement cures, leaving behind a solid structure. It should be understood that an inflatable device could have walls constructed of a combination of elastomeric and non-elastomeric components to allow expansion in controlled directions. This association of differing components allows the device to function simultaneously as a tool for disc space height restoration, and allows for the use of a very complex device geometry that can be recreated in situ.

The space within the chamber is then filled with bone and/or biologics that intimately contact both endplates to permit bony fusion. The biologics may be, for example, cancellous bone.

In either iteration, if a single chamber is used, it roughly takes the form of a doughnut shape, i.e., toroidal. The chamber may have a crossing strut for added strength and/or a crossing or circumferential wire, cable, or filament to enhance tensile strength, since most hardenable resins are notably weaker when subject to a tensile force. The center part of the doughnut defines the space or spaces where bone or biologic fusion products are injected. Obviously, any shape could be employed, however, the preferred embodiment comprises a shape that approximates the shape defined by the perimeter of the vertebral body endplate (i.e., modified toroidal) and is similar to presently implanted monolithic anterior lumbar interbody fusion prostheses made of titanium or PEEK, rather than being a simple amorphous donut shaped sac into which a hardenable material is injected.

If two or more inflatable chambers are placed, the preferred embodiment allows the chambers to interdigitate or lock together like puzzle pieces to limit independent motion each from the other. Such a set up might be employed when a single chamber inflatable prosthesis is too large, even in its deflated state, to be inserted down the working chamber of an endoscope. In this scenario, the first chamber is placed endoscopically, followed by the second chamber and then both are inflated to restore disc space height and to define an intervening space or cavity for the placement and containment of bone or biologic fusion products.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 17A shows an embodiment of an expandable intervertebral fusion implant, in an uninflated state, as a nontoroidal shaped cage having surface studs;

FIG. 17B shows the partially inflated expandable intervertebral fusion implant of FIG. 17A;

FIG. 17C shows the fully inflated expandable intervertebral fusion implant of FIG. 17A;

FIG. 19A shows an embodiment of an expandable intervertebral fusion implant, in an uninflated state, as a non-toroidal inflatable cage having cable and filament enhancement;

FIG. 19B shows the partially inflated expandable intervertebral fusion implant of FIG. 19A; and, FIG. 19C shows the fully inflated expandable intervertebral fusion implant of FIG. 19A defining two cavities for containment of biologics material.

DETAILED DESCRIPTION

Figure 1:
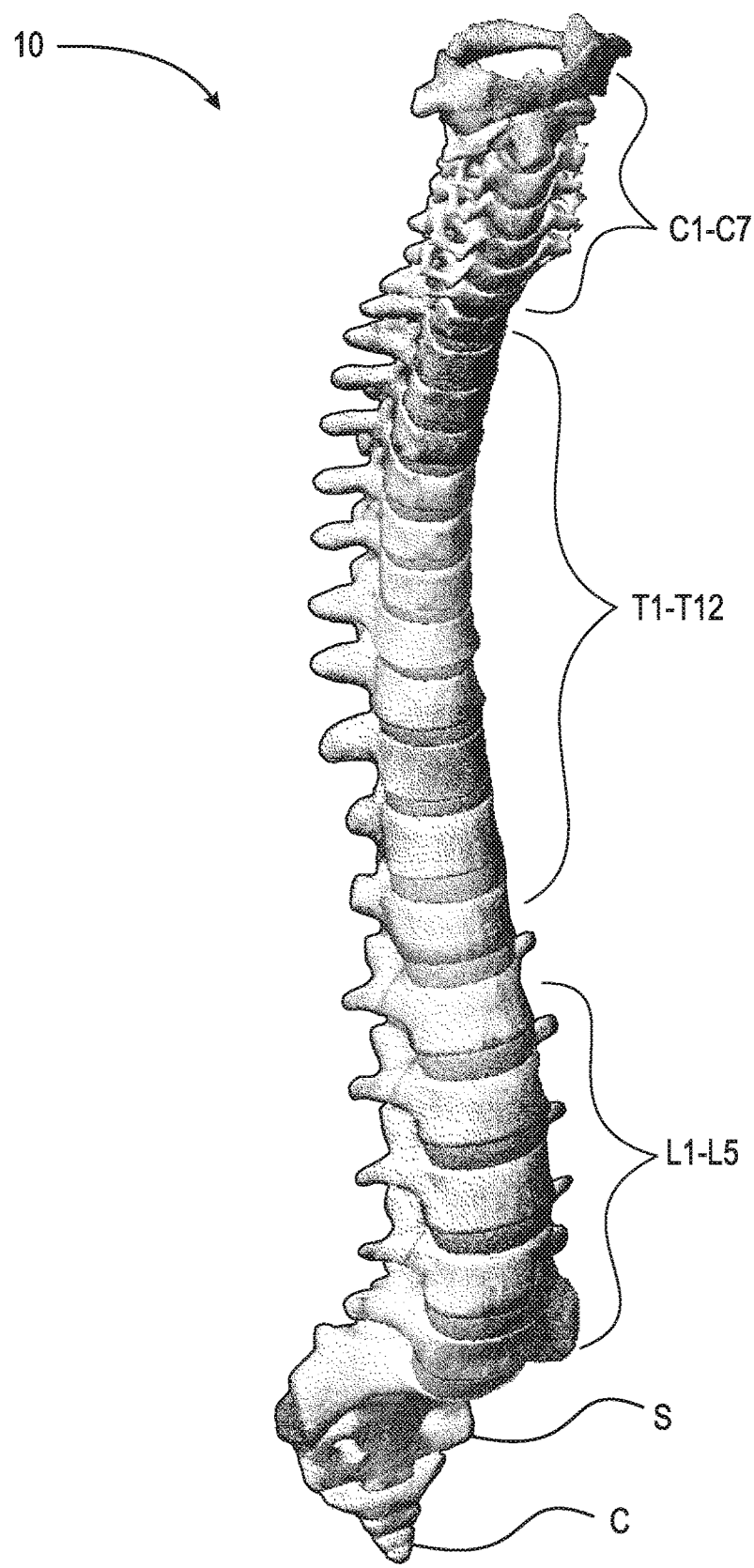
FIG. 1 is an anterior perspective view of a spinal column.
Figure 2:
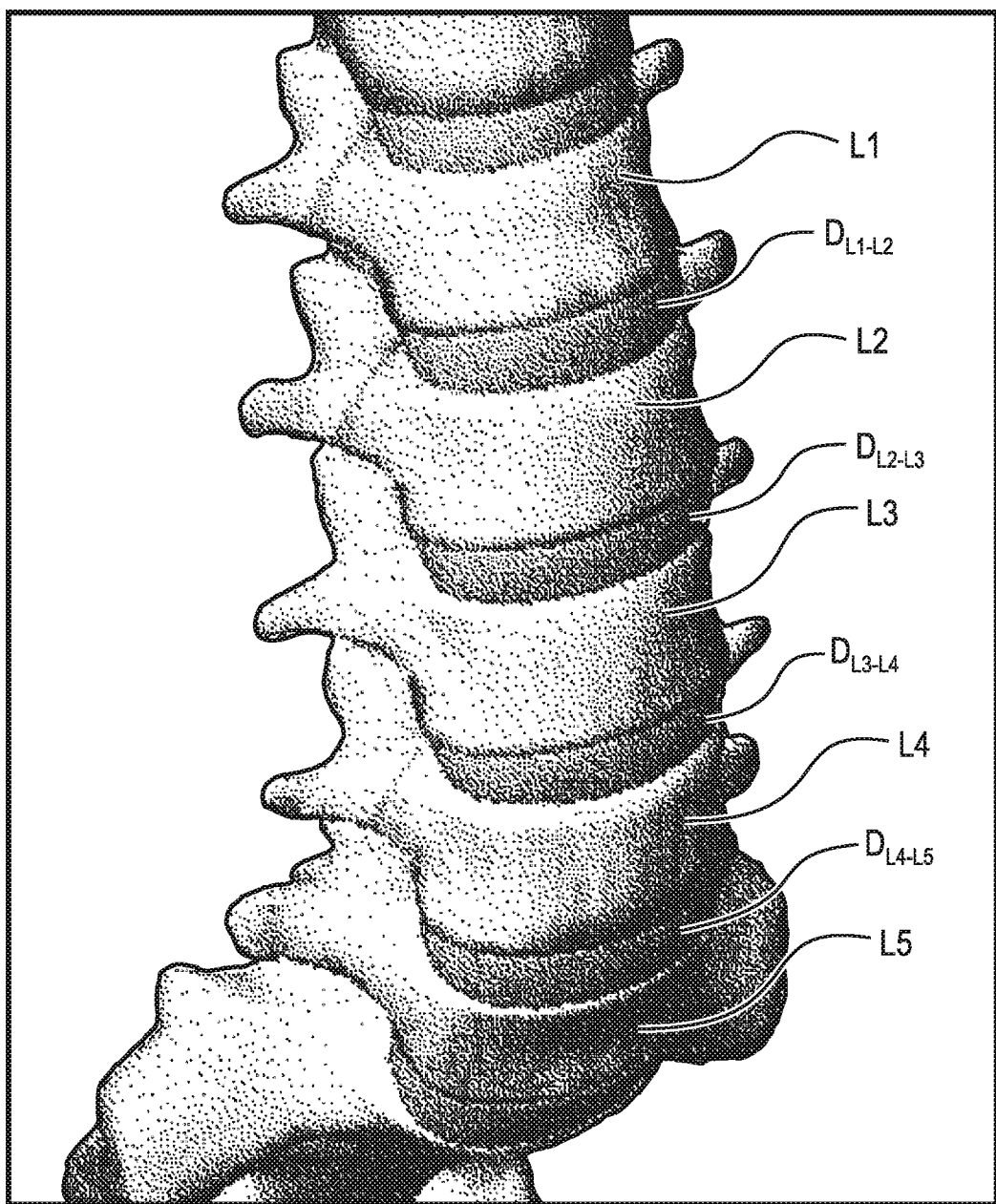
FIG. 2 is an anterior perspective view of the lumbar section of the spinal column shown in FIG. 1.
Figure 3:
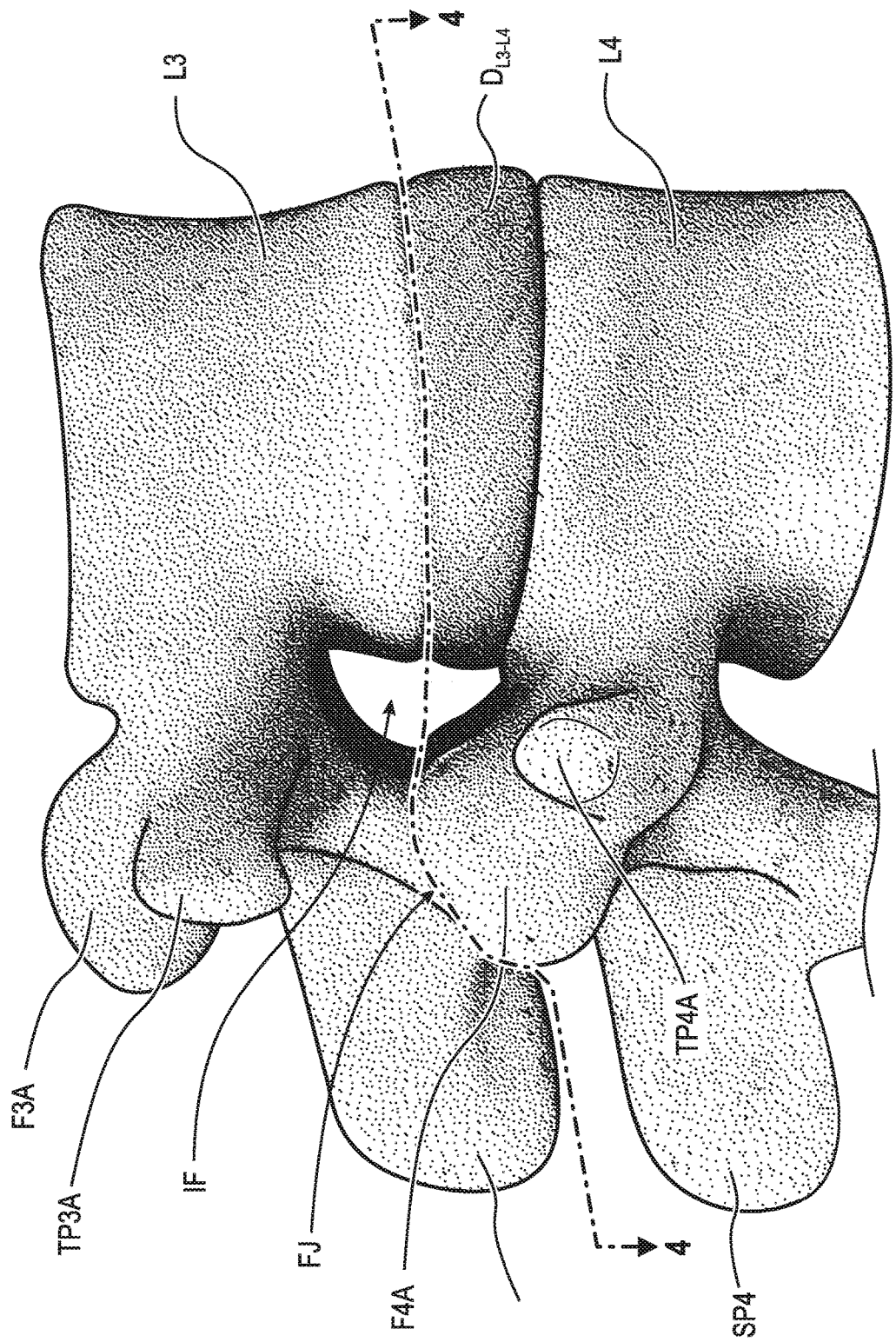
FIG. 3 is a lateral perspective view of two vertebrae, a disc, and related spinal anatomy.
Figure 4:
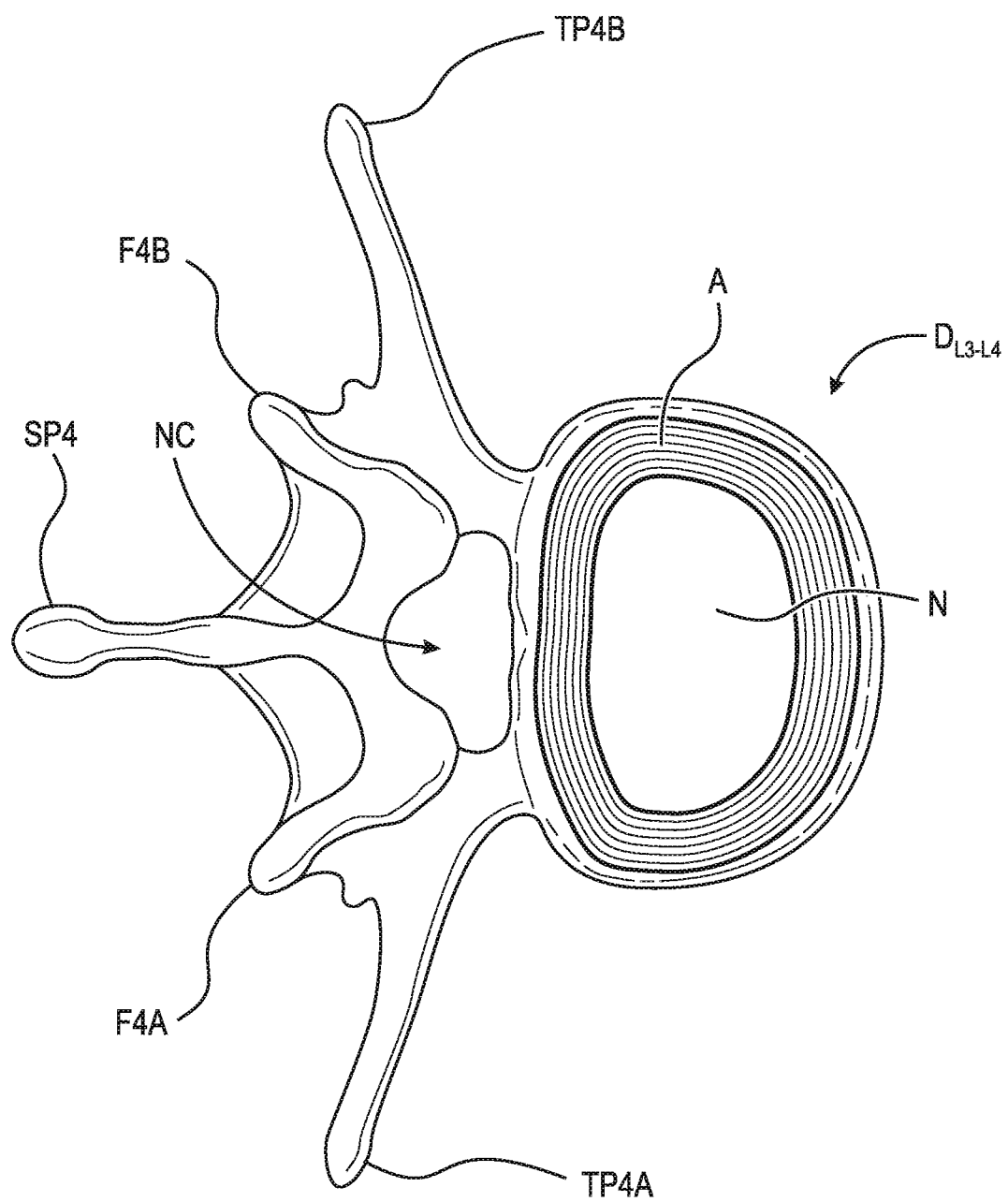
FIG. 4 is a top view of a section of the spinal column, taken generally along line 4-4 in FIG. 3.
Figure 5:
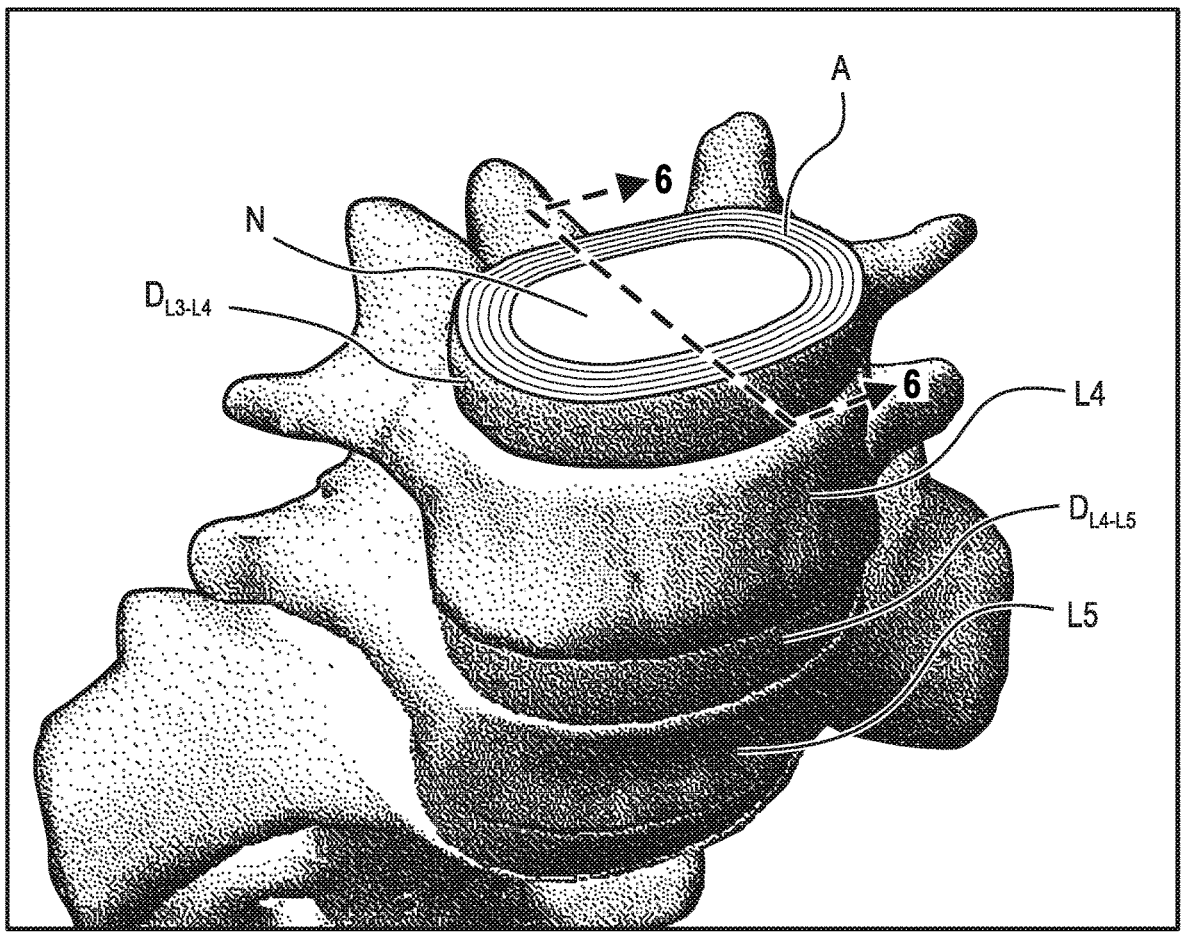
FIG. 5 is an enlarged anterior perspective view of the spinal column shown in FIG. 2, except with the top vertebra and all other structure above the top vertebra removed.
Figure 6:
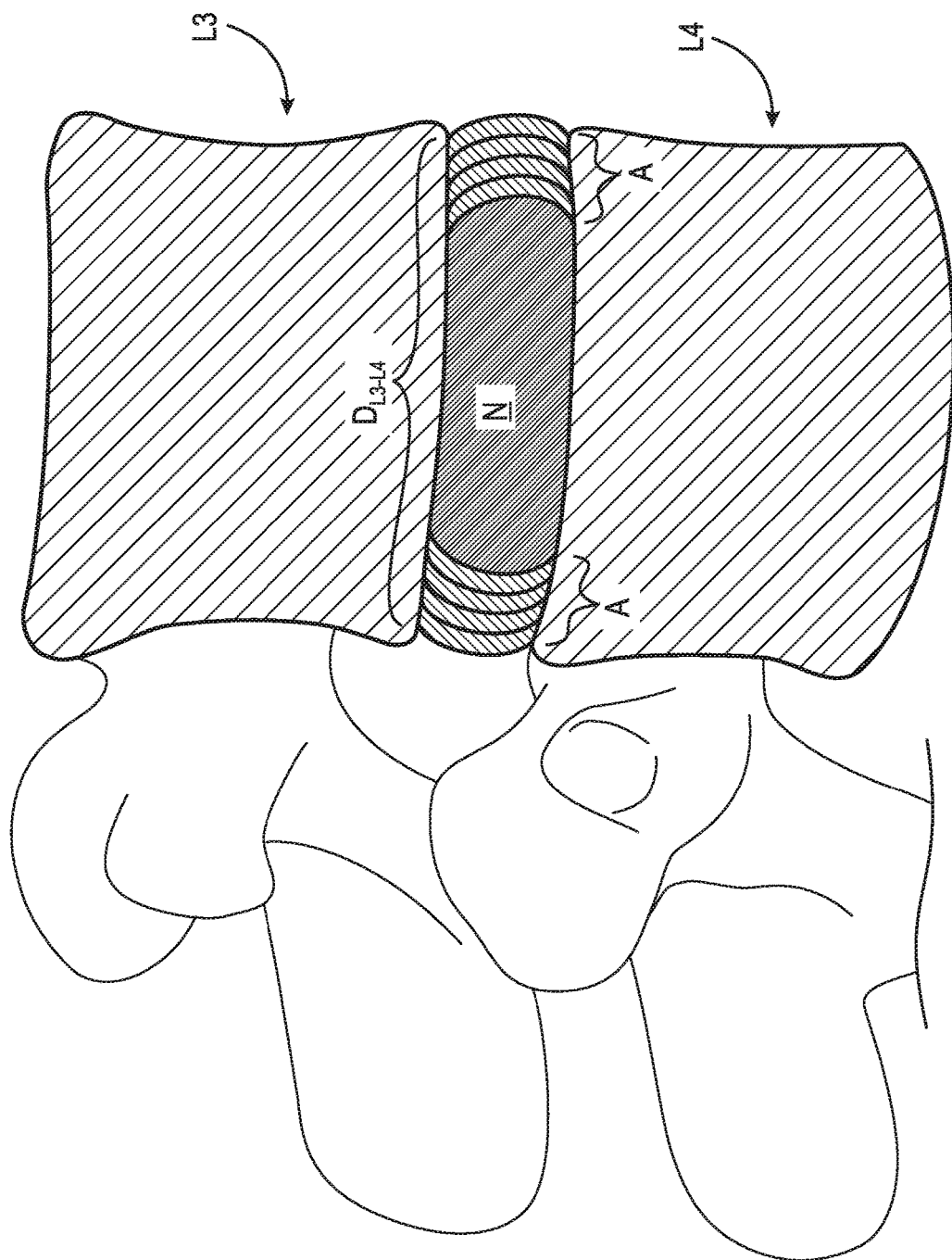
FIG. 6 is a partial cross-sectional view of the top and bottom vertebrae and disc, taken generally along line 6-6 in FIG. 5.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, and/or pneumatics.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

The term "balloon" as used in the present disclosure is intended to mean any inflatable member which can be elastomeric or non-elastomeric or combination thereof and made of any suitable material.

The drawings show several embodiments having the salient feature that each implantable prosthesis or implant has at least one inflatable chamber capable of being injected with a hardenable material that enlarges the implant to a functional size and shape. The material then hardens to form a permanent endoprosthesis within an intervertebral disc space suitably prepared for interbody fusion. The volume of hardenable material to be used is determined by volume, by injection pressure, or by a combination of the two parameters. These parameters can be assessed prior to final implantation by injecting a radioopaque contrast media which can be visualized under a fluoroscope, measured, and removed. The removed volume approximates the hardenable material to be injected. Fluoroscopically, visualized restoration of disc height or vertebral lithesis could also be used to gauge how much hardenable material to inject.

The preferred embodiment comprises one of two basic iterations; elastomeric or non-elastomeric. However, it should be understood that an endoprosthesis could employ both characteristics in the same device. For example, a device with non-elastomeric sidewalls but elastomeric top and bottom surfaces would allow biased expansion vertically but not horizontally. Non-elastomeric strings, cables, wires, or filaments may also be employed to connect the inner walls of the chambers thereby limiting expansion in certain directions allowing for shape changes with expansion and to serve or aid in the strengthening of the construct much like rebar does to cement. These filaments could be made of, inter alia, polymer, metal, carbon fiber, etc.

The elastomeric version comprises a distensible chamber, the walls of which are elastomeric allowing them to expand in multiple directions at once, much like a latex balloon. This iteration would be preferred when the implant is to be placed down the working channel of an endoscope because its elastomeric nature lends itself more readily to a very small size on initial insertion since expansion of the chamber walls occur in conjunction with expansion of the chamber cavity as the device is filled with a hardenable material. Once one or more chambers are inflated to the appropriate size, as determined by measured volume, injection pressure, or by fluoroscopy, and a constant pressure is maintained on the injected material until it hardens and remains fixed as a permanent implant. The injection tube or cannula is then detached leaving the formulated endoprosthesis in situ. In this version, it may be preferential to place bone putty or biologics in the interspace defined by the chamber prior to inflation as expansion of the device compresses the space available for biologic fusion material thereby forcing the fusion material against the prepared endplates and hence facilitating and accelerating fusion by Wolff s law.

The second iteration comprises non-elastomeric sidewalls such that the device forms a largely predetermined final shape and size once injected with hardenable material. A simple analogy would be an inflatable pool or zodiac boat which assumes a fixed predetermined size and shape once fully inflated. This iteration could be formulated in shapes of essentially infinite dimensions and complexities. In this iteration, the final shape of the device can conform to the shape of any existing implantable interbody fusion device presently employed for such purposes. Any shape and size can be replicated by using preset dimensions of the various chamber walls. The collapsed implant would then be inserted via an endoscope into an intervertebral disc space suitably prepared for interbody fusion and inflated to its final shape and form ready to be filled with biologics to facilitate fusion. Because the implant is inflated to its final implant size and shape in situ, it can reliably and safely be implanted endoscopically since the final size and shape is altered and/or magnified many times when compared to its insertional dimensions.

One or more of these inflatable fusion implants can be inserted into a disc space entirely via an endoscope so that the shape and function of presently available implantable devices can be fully replicated, but without the large incision and dissection required to achieve implantation.

In either iteration, the cannula or tube used to inflate the implant is detachable, with or without a valve. Suitable valves would be a Presta valve or a Schrader valve, but because the injected material is hardenable, a valve system may not always be necessary. The tube valve connection comprises a male/female threaded or Luer Lock linkage disconnected by twisting the inflating tube or cannula, once the hardenable material has set.

Figure 7:
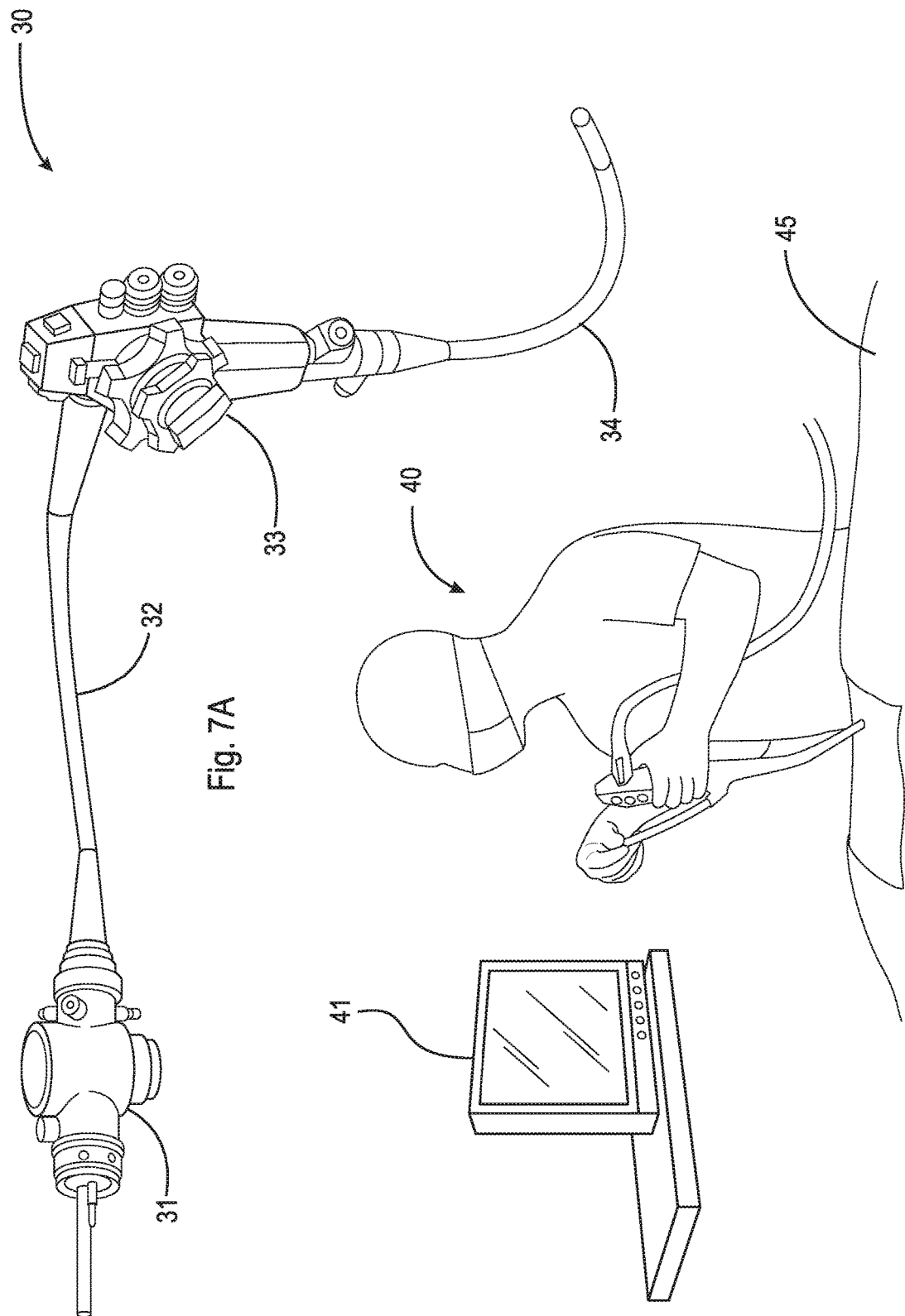
FIG. 7A is a view of a typical endoscope.
FIG. 7B illustrates use of the endoscope shown in FIG. 7A by a surgeon performing a discectomy (diskectomy).

Adverting now to the figures, and as described previously, FIGS. 1-6 depict various parts and sections of spinal anatomy, and FIGS. 7A and 7B depict a typical endoscope for use by a surgeon on a patient.

Figure 8:
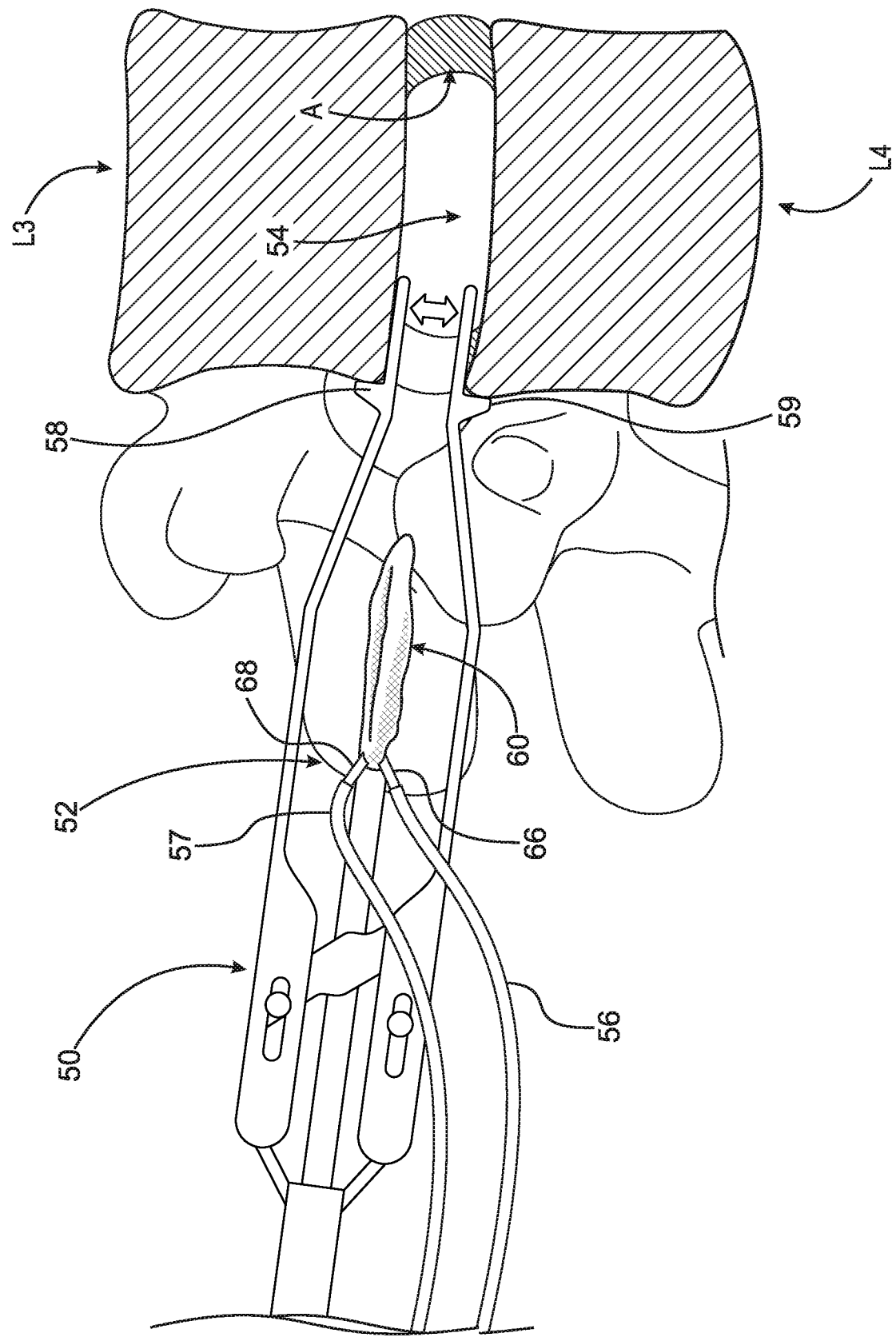
FIG. 8 illustrates a preliminary step in an intervertebral fusion implant procedure, namely, the introduction of a distractor to the disc space.
Figure 9:
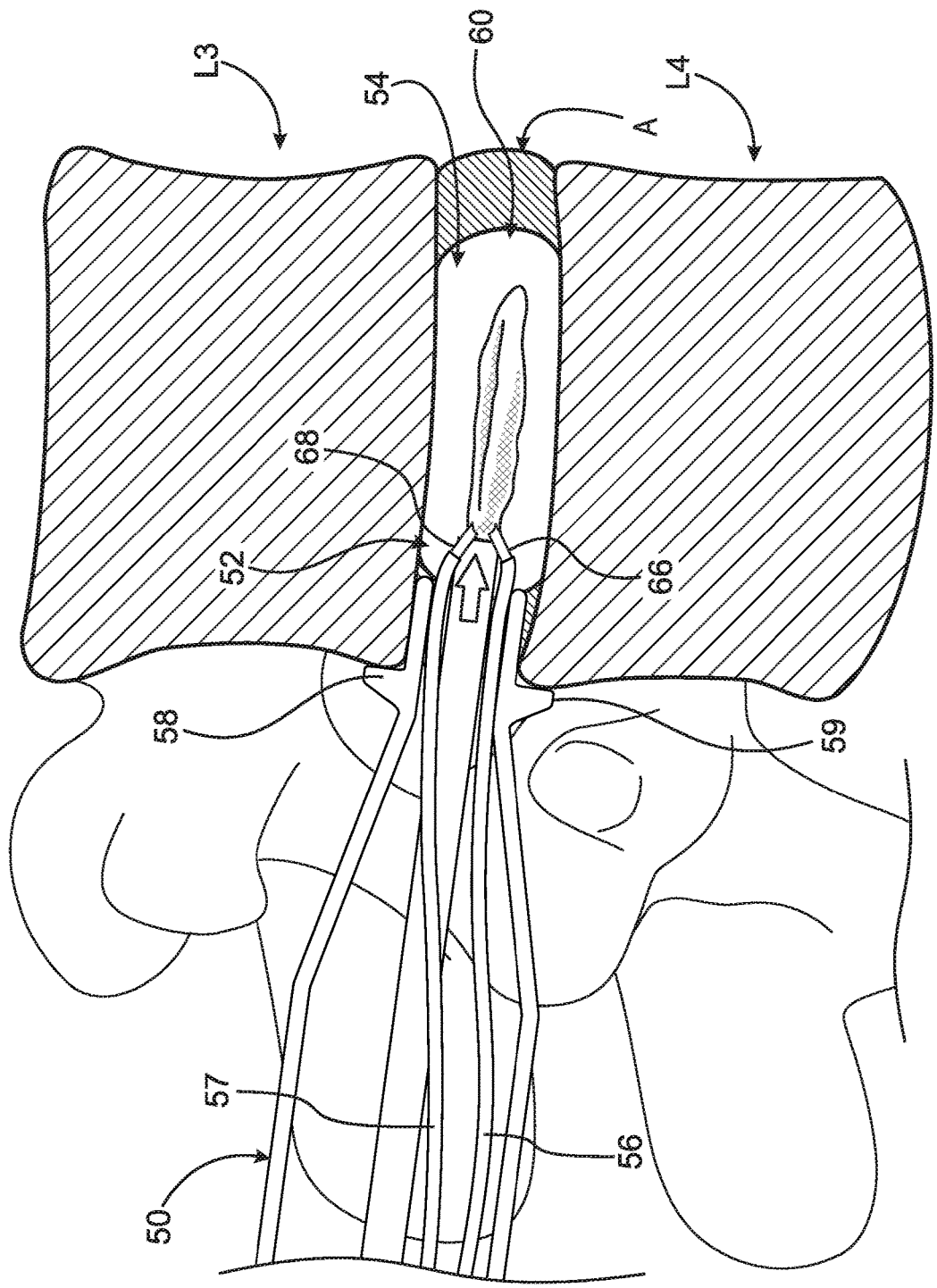
FIG. 9 illustrates the introduction of an expandable intervertebral fusion implant into the disc space using a distractor with the implant in an unexpanded state.
Figure 10:
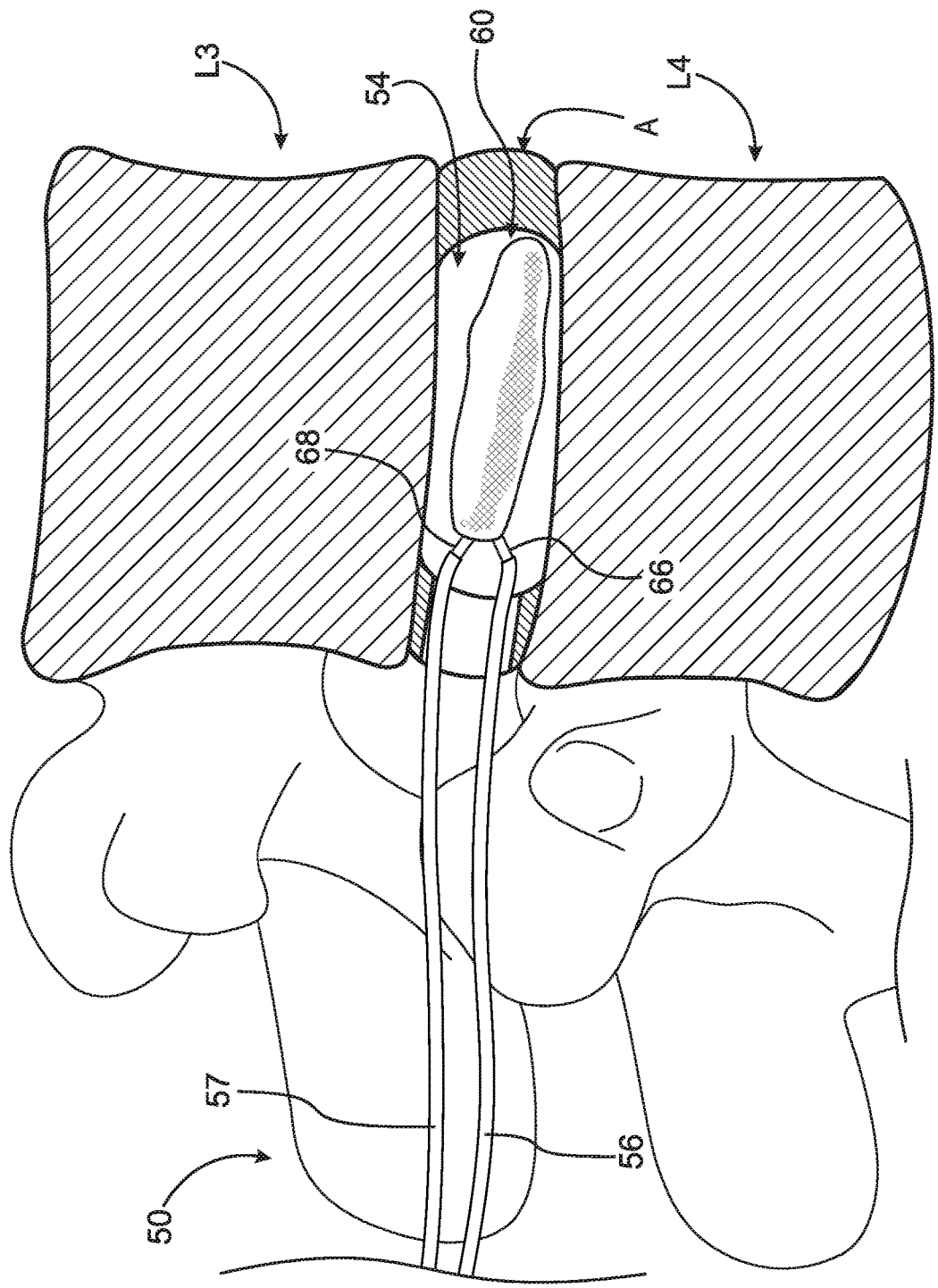
FIG. 10 illustrates the intervertebral fusion implant in place in the disc space, in a partially expanded state.
Figure 11:
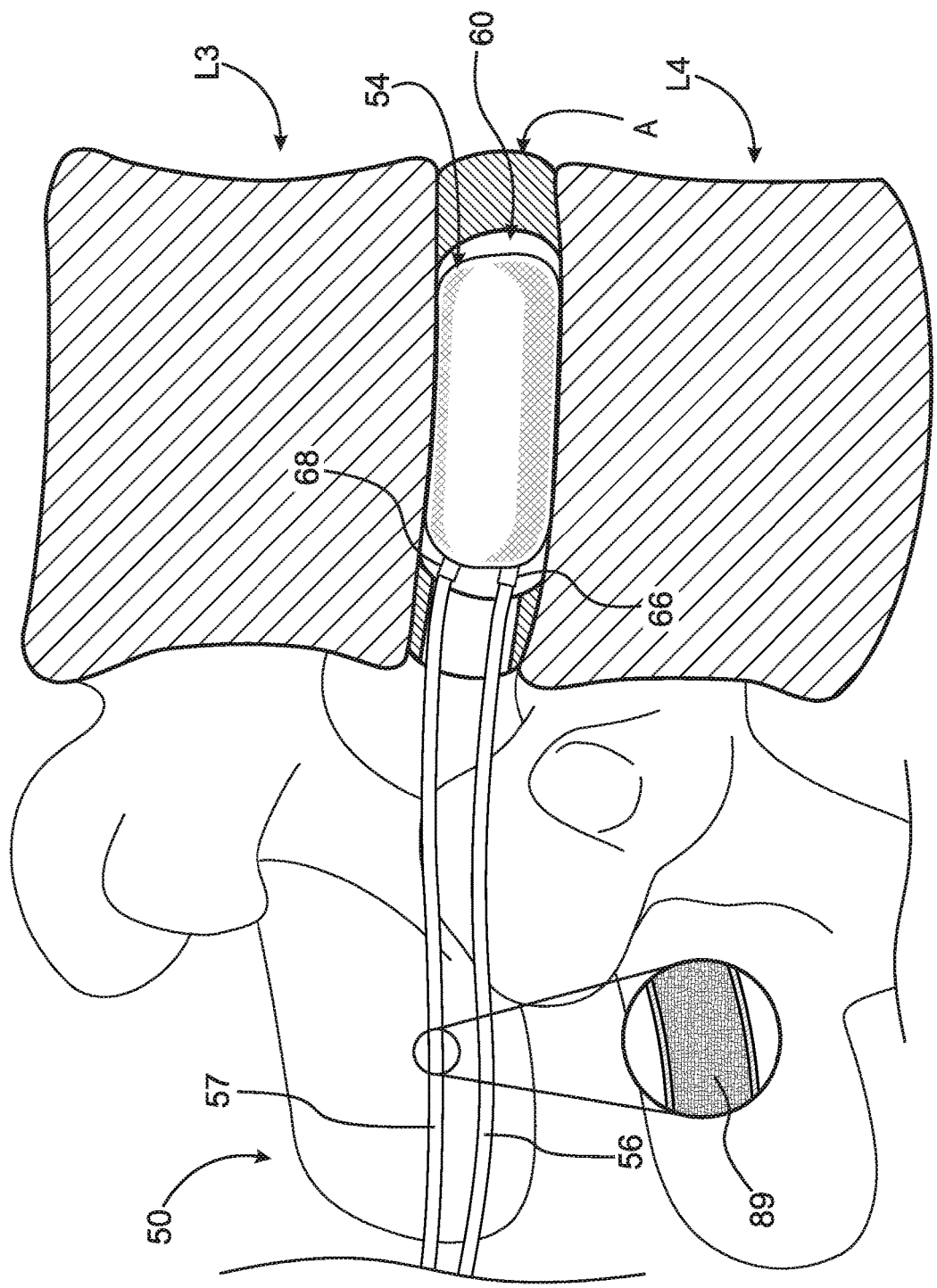
FIG. 11 illustrates the expandable intervertebral fusion implant in place in the disc space, in a fully expanded state.
Figure 12:
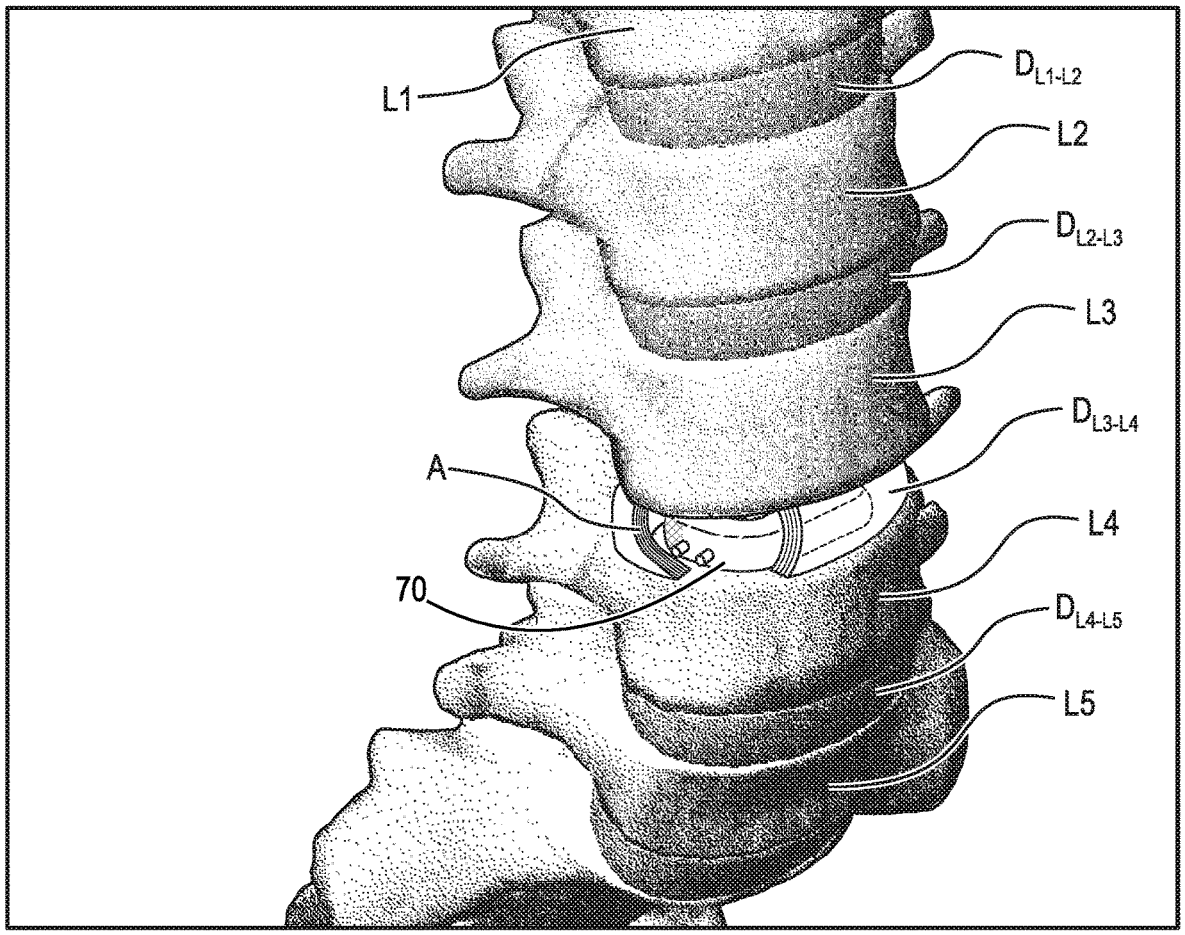
FIG. 12 is an anterior perspective view of a spinal column including the expandable intervertebral fusion implant shown in FIG. 11.

FIGS. 8 and 9 illustrate introduction of disc space distractor 50. Distractor 50 is used to maintain distance between vertebrae L3 and L4 and insert expandable intervertebral fusion implant 60 into disc space 54 between the above-mentioned vertebrae. Disc space distractor 50 includes spacers 58 and 59. Distractor secures implant 60 for insertion through means of attachment 52. Means of attachment 52 comprises any suitable means for securely placing implant 60 between vertebrae L3 and L4, such as tongs, suction cups, threaded couplings or other mechanical couplings, etc. Upper spacer 58 is placed between L3 and L4 and contacts vertebra L3. Lower spacer 59 is placed between L3 and L4 and contacts vertebra L4. Spacers 58 and 59 are then separated to enlarge disc space 54. Once disc space 54 is large enough, implant 60 may be introduced in an unexpanded state. It should be understood that any suitable tool can be used to maintain distance between the vertebrae and insert the implant. Injection cannula 68 is connected to implant 60. Injection tube 57 is connected to injection cannula 68. Biologics port 66 is connected to implant 60. Injection tube 56 is connected to biologics port 66. FIG. 10 illustrates implant 60 in disc space 54, in a partially expanded state. FIG. 11 illustrates implant 60 in disc space 54, in a fully expanded state. Hardenable material is fed through injection tube 57 and injection cannula 68 into implant 60. Pressure may be maintained within injection tube 57 while hardenable material 89 is hardening, so as to maintain the desired shape of implant 60 between vertebrae L3 and L4. Once hardenable material 89 hardens in implant 60, injection cannula 68 can be removed from implant 60. FIG. 12 is an anterior perspective view of spinal column 10 including expandable intervertebral fusion implant 70. In this embodiment, implant 70 is an inflatable cage.

Figure 13A:
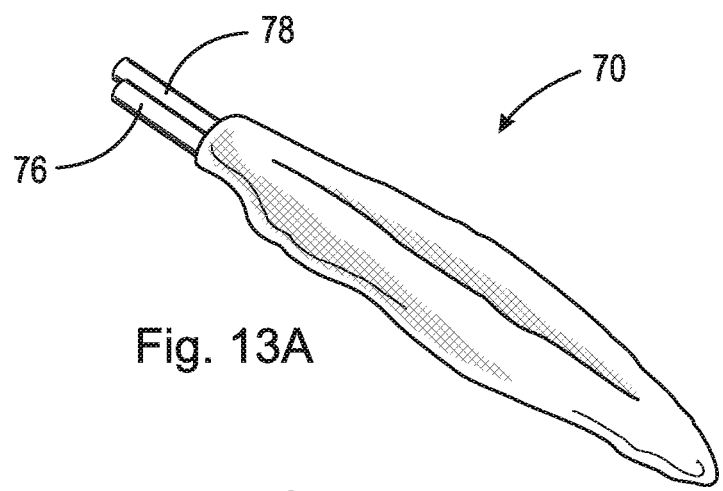
FIG. 13A depicts an uninflated expandable intervertebral fusion implant ready for insufflation.
Figure 13B:
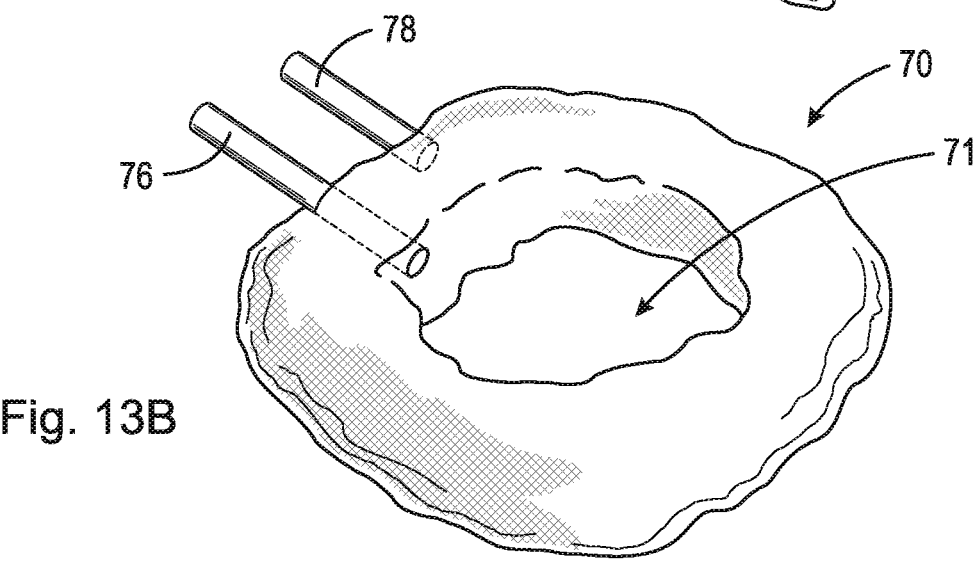
FIG. 13B shows the partially inflated expandable intervertebral fusion implant of FIG. 13A with injection cannula and biologics port.
Figure 13C:
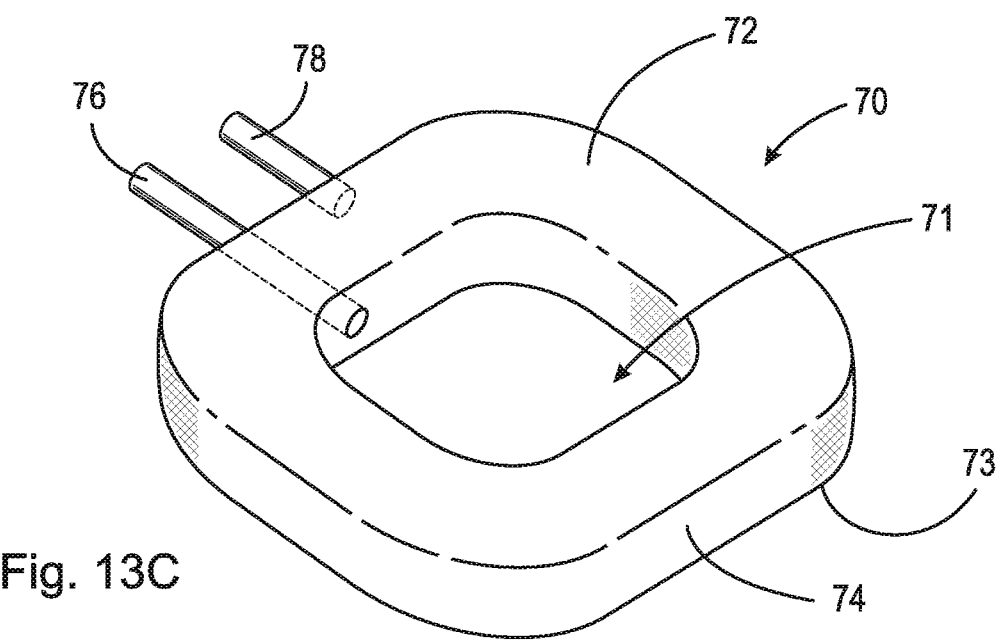
FIG. 13C shows the fully inflated expandable intervertebral fusion implant of FIG. 13A with a defined cavity for biologics material.

FIG. 13A depicts uninflated implant 70 with injection cannula 78 ready for insufflation. FIG. 13B shows a partially inflated implant 70 with injection cannula 78 for injection of hardenable material and biologics port 76 for injection of biologics. Biologics port 76 extends into cavity 71 of implant 70. FIG. 13C shows a fully inflated implant 70 with defined cavity 71 for biologics. When fully insufflated with hardenable material, implant 70 is toroidal shaped and comprises top surface 72, bottom surface 73, and wall 74. Surfaces 72 and 73 are generally perpendicular to wall 74, and cavity 71 extends from top surface 72 to bottom surface 73.

Figures 14A, 14B:
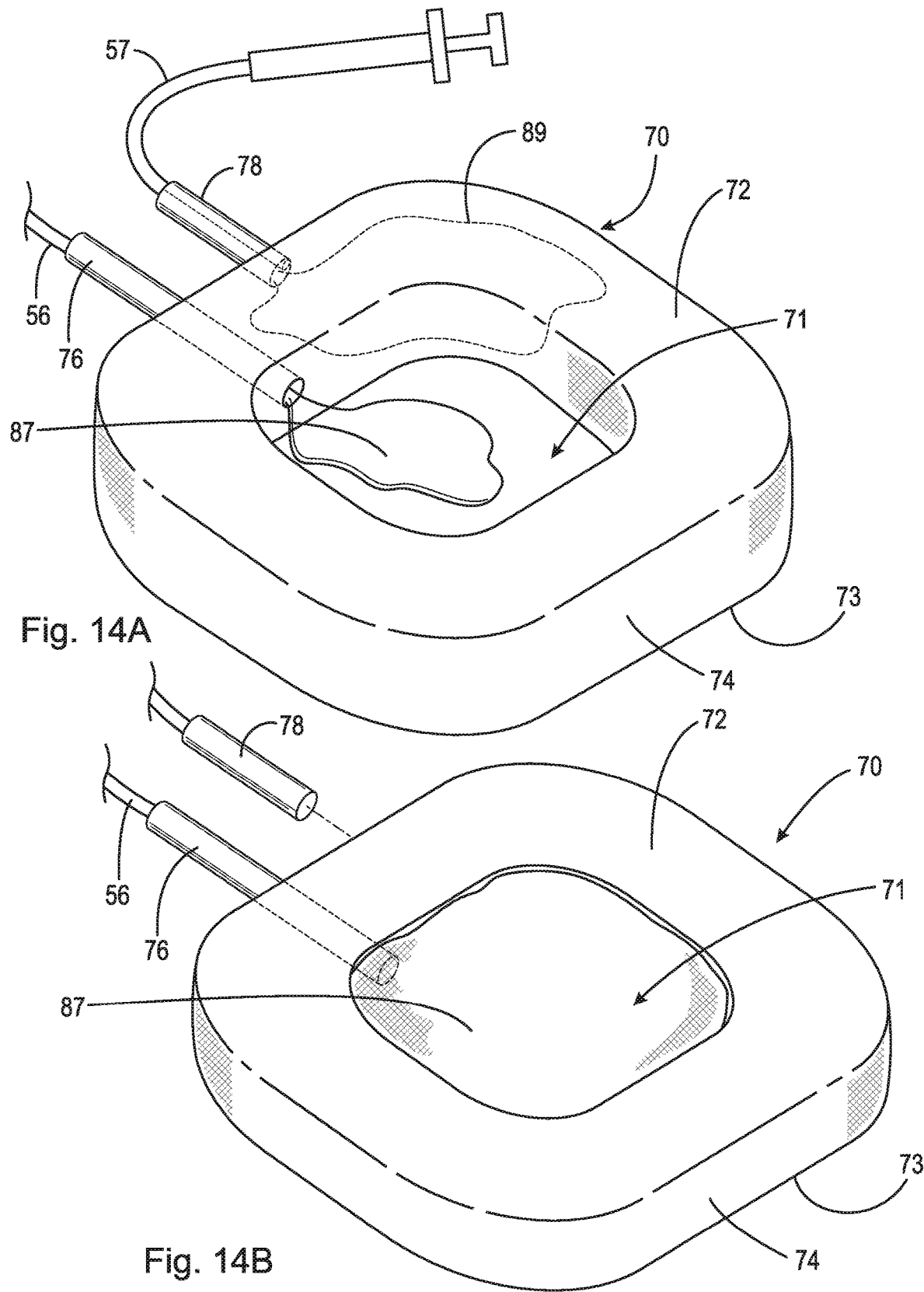
FIG. 14A is an enlarged view of a fully inflated expandable intervertebral fusion implant with hardenable material and biologics material being injected.
FIG. 14B is an enlarged view of a fully inflated expandable intervertebral fusion implant now turgid with hardenable material ready to set into solid form, with the injection cannula disconnected.

FIG. 14A is an enlarged view of a fully inflated implant 70 with hardenable material 89 being injected into implant 70 through injection tube 57 and injection cannula 78. Once implant 70 is fully insufflated, biologics material 87 is injected into cavity 71 through injection tube 56 and biologics port 76. FIG. 14B is an enlarged view of a fully inflated implant now turgid with hardenable material 89 ready to set into solid form, biologics material 87 ready to fuse vertebrae, and injection cannula 78 disconnected from implant 70.

Figure 15A:
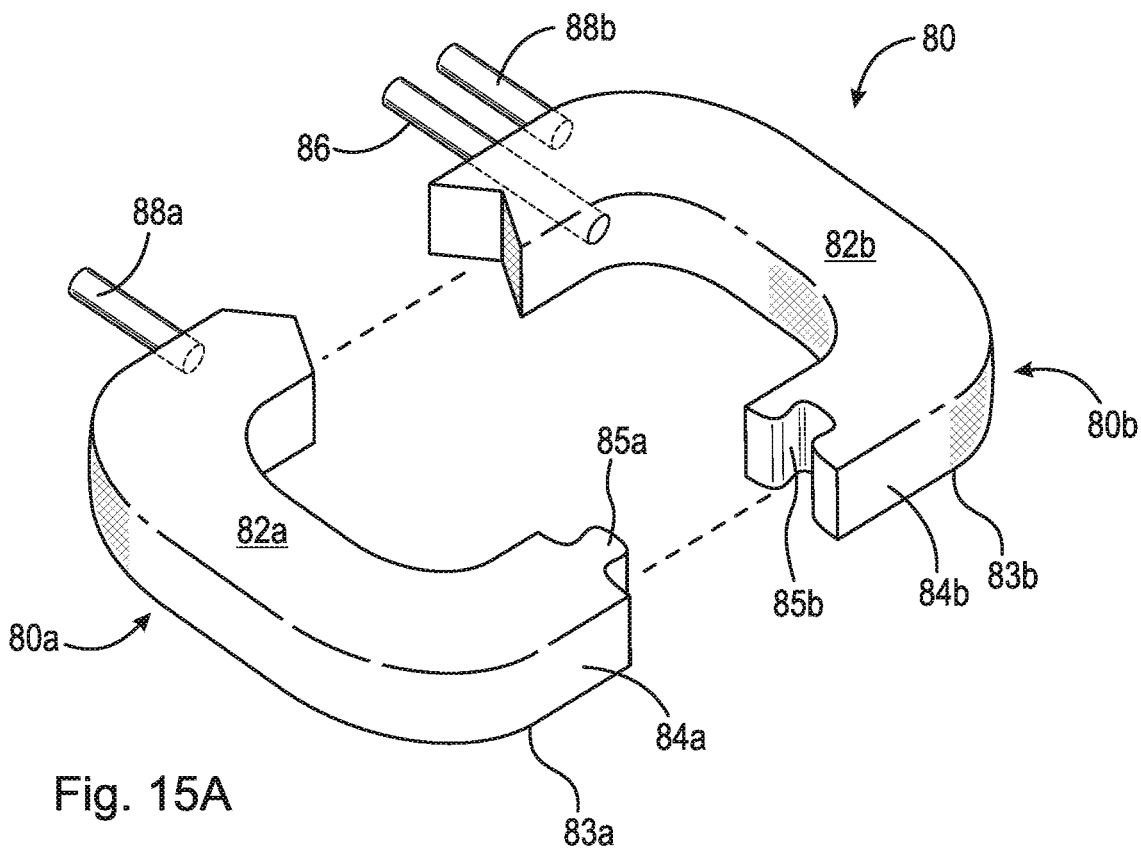
FIG. 15A shows an embodiment of an expandable intervertebral fusion implant as an inflatable cage formed by two separate inflatable components.
Figure 15B:
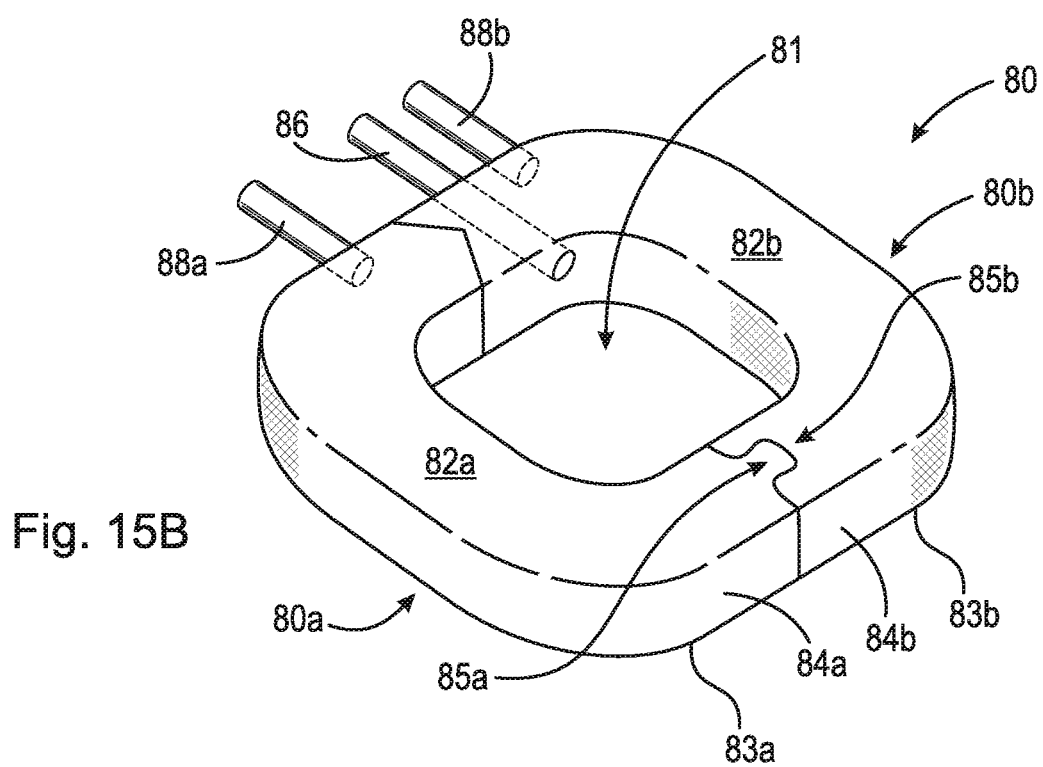
FIG. 15B shows the fully inflated version of the expandable intervertebral fusion implant shown in FIG. 15A with first and second portions interlocked and defining a cavity for insertion of biologics material.

FIG. 15A shows an embodiment of implant 80 as an inflatable cage formed by two separate inflatable components. Implant 80 is toroidal shaped and comprises first portion 80a and second portion 80b. First portion 80a comprises top surface 82a, bottom surface 83a, wall 84a, male connector 85a, and injection cannula 88a. Second portion 80b comprises top surface 82b, bottom surface 83b, wall 84b, female connector 85b, injection cannula 88b, and biologics port 86. It should be appreciated that biologics port 86 may be connected to first portion 80a instead of second portion 80b. FIG. 15B shows the fully inflated version of implant 80 with first and second portions 80a and 80b interlocked and defining cavity 81 for insertion of biologics. Male connector 85a locks with female connector 85b. It should be appreciated that any suitable connectors may be used to connect first portion 80a with second portion 80b. Hardenable material 89 is injected into first portion 80a and second portion 80b through injection cannulas 88a and 88b, respectively. Once first and second portions 80a and 80b are connected and fully insufflated, biologics material 87 is injected into cavity 81 through biologics port 86.

Figure 16A:
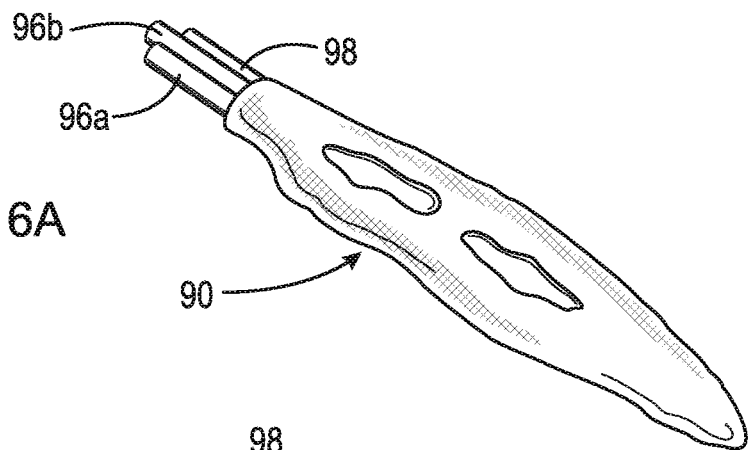
FIG. 16A shows an embodiment of an expandable intervertebral fusion implant as a nontoroidal shaped cage in a uninflated state.
Figure 16B:
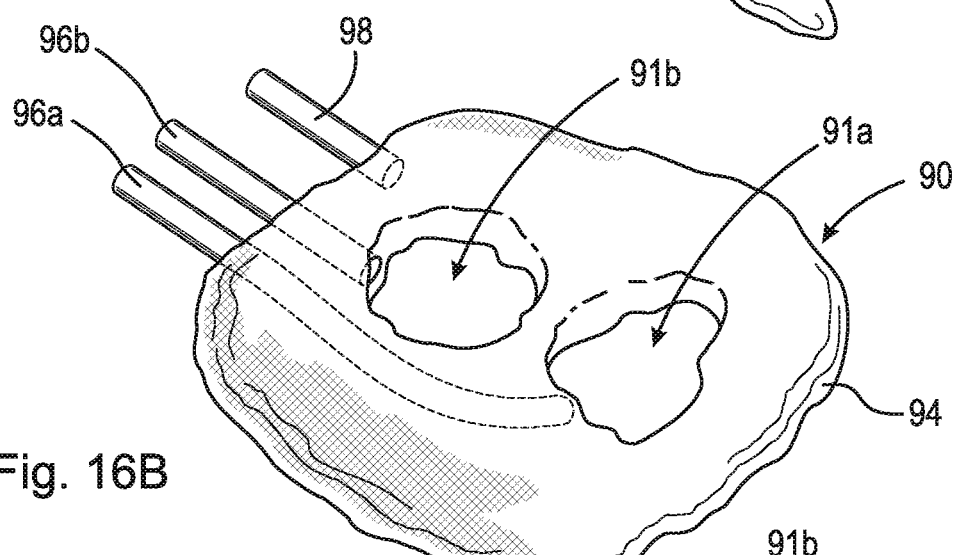
FIG. 16B shows the partially inflated expandable intervertebral fusion implant of FIG. 16A.
Figure 16C:
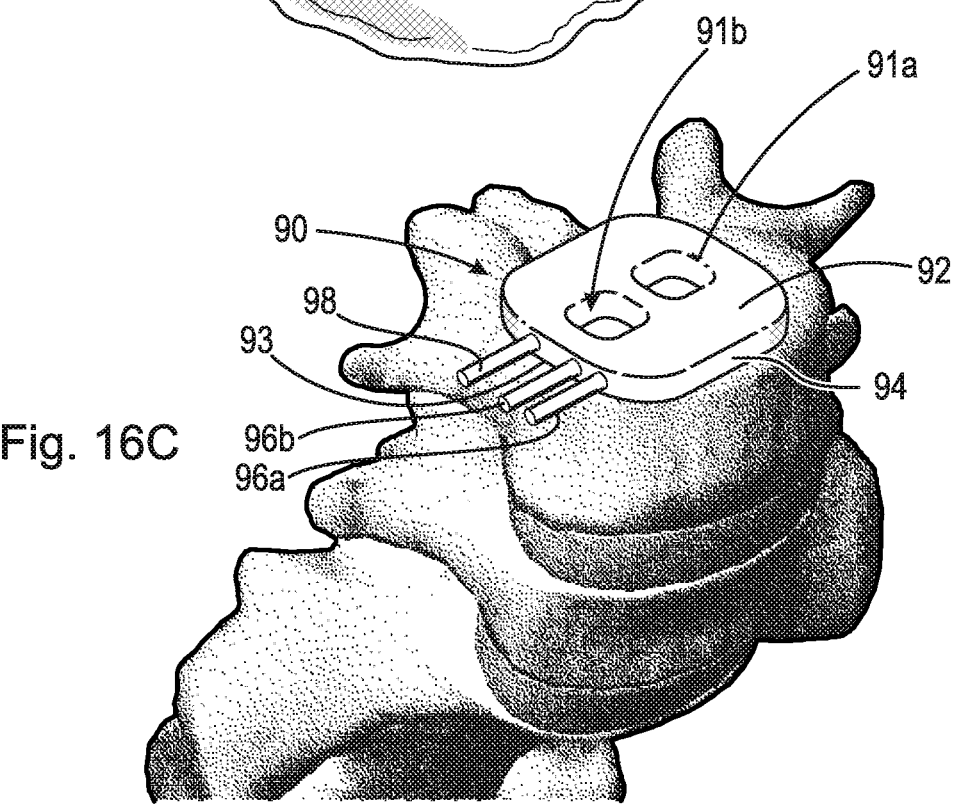
FIG. 16C shows the fully inflated expandable intervertebral fusion implant of FIG. 16A in situ defining two separate cavities for insertion of biologics material.

FIG. 16A shows an embodiment of implant 90 as a nontoroidal shaped cage in an uninflated state. FIG. 16B shows a partially inflated implant 90. FIG. 16C shows the fully inflated implant 90 in situ defining two separate cavities for insertion of biologics. Implant 90 comprises cavities 91a and 91b, top surface 92, bottom surface 93, wall 94, biologics ports 96a and 96b, and injection cannula 98. Cavities 91a and 91b extend from top surface 92 to bottom surface 93. Hardenable material 89 is injected into implant 90 through injection cannula 98. Biologics material 87 is injected into cavities 91a and 91b through biologics ports 96a and 96b, respectively. Injection cannula 98 is removable from implant 90 after hardenable material 89 has hardened.

FIG. 17A shows an embodiment of implant 100, in an uninflated state, as a nontoroidal shaped cage having surface studs embedded on the surfaces to facilitate interdigitation with the vertebral endplate. The studs fix the endoprosthesis in position and retard migration. FIG. 17B demonstrates a further stage of inflation of implant 100. FIG. 17C demonstrates the fully inflated implant 100. Implant 100 comprises cavities 101a and 101b, top surface 102, bottom surface 103, wall 104, biologics ports 106a and 106b, and injection cannula 108. Cavities 101a and 101b extend from top surface 102 to bottom surface 103. Hardenable material 89 is injected into implant 100 through injection cannula 108 (not shown). Biologics material 87 is injected into cavities 101a and 101b through biologics ports 106a and 106b, respectively (not shown). Injection cannula 108 is removable from implant 100 after hardenable material 89 has hardened. Top and bottom surfaces comprise a plurality of studs 105.

Figure 18A:
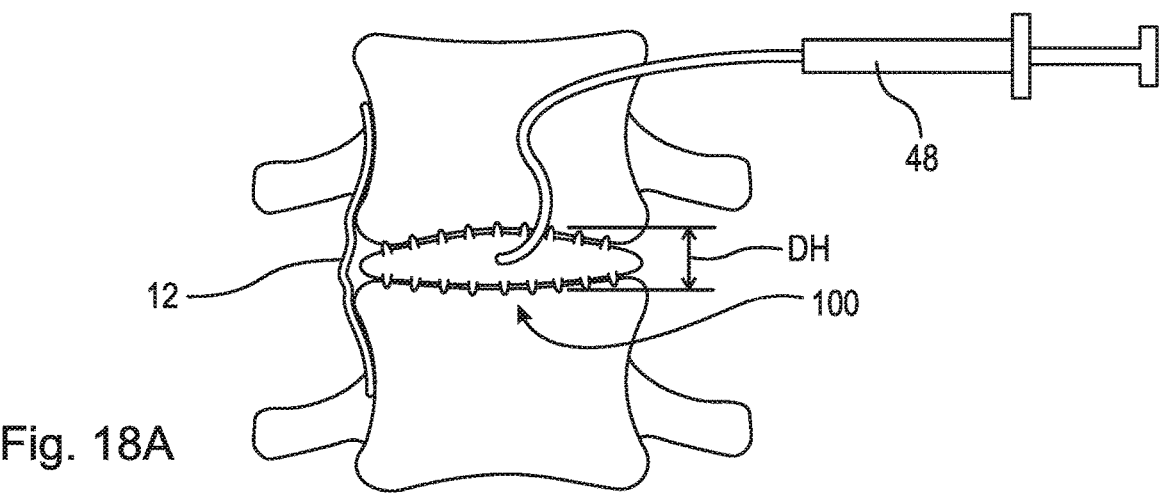
FIG. 18A schematically demonstrates the expandable intervertebral fusion implant of FIG. 17A in situ partially filled with hardenable material.
Figure 18B:
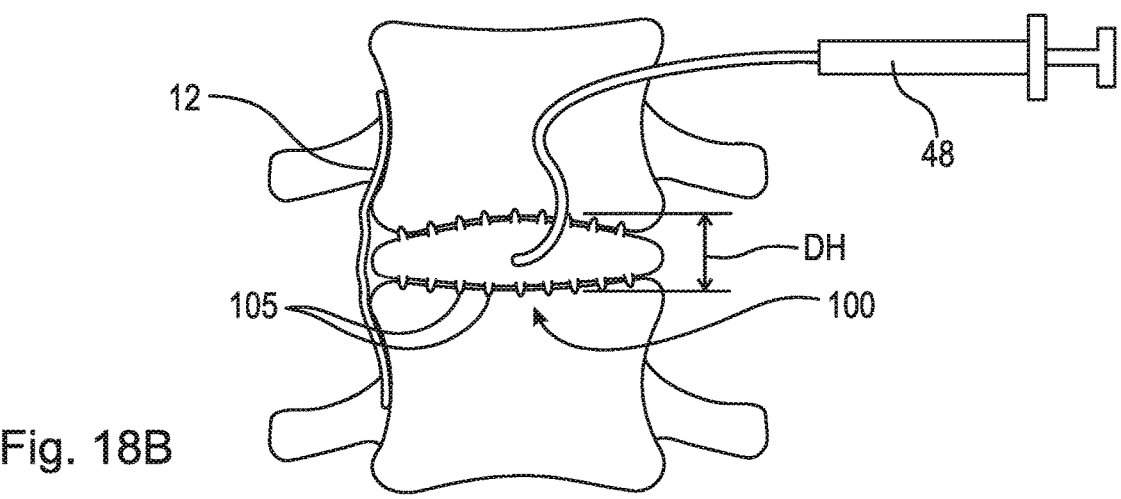
FIG. 18B schematically demonstrates further inflation of the expandable intervertebral fusion implant of FIG. 17A with partial tautening of ligaments and partial restoration of disc space height.
Figure 18C:
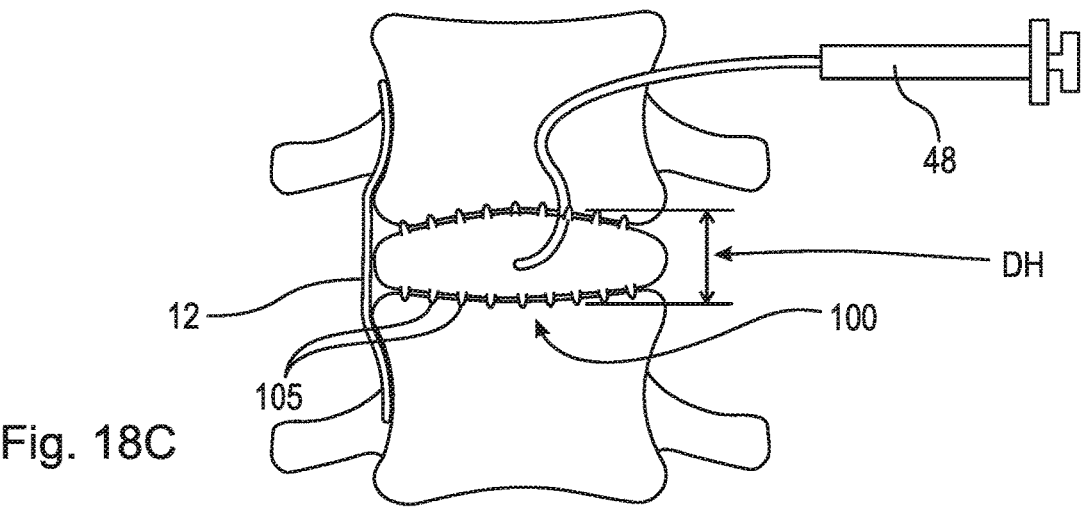
FIG. 18C schematically demonstrates the fully inflated expandable intervertebral fusion implant of FIG. 17A with full restoration of disc space height and fully tautened ligaments.

FIG. 18A schematically demonstrates implant 100 in situ partially filled with hardenable material 89 (not shown). FIG. 18B schematically demonstrates further inflation of implant 100 with partial tautening of ligament 12 and partial restoration of disc space height DH. FIG. 18C schematically demonstrates a fully inflated implant 100 with full restoration of disc space height DH and fully tautened ligament 12 as well as showing surface studs 105 engaging the endplate for added stability and to resist migration of implant 100. As injector 48 injects hardenable material 89 (not shown) into implant 100, disc space height DH increases thereby tautening ligament 12. This sequence is illustrated in FIGS. 18A-C.

FIG. 19A shows an embodiment of implant 110, in an uninflated state, as a nontoroidal inflatable cage defining two cavities for insertion of biologics and having cable and filament enhancement. FIG. 19B shows implant 110 in an intermediate stage of inflation. FIG. 19C shows a fully inflated implant 110 defining two cavities for containment of biologics. Implant 110 comprises cavities 111a and 111b, top surface 112, bottom surface 113, wall 114, biologics ports 116a and 116b, injection cannula 118, filaments 120 and 121, and perimeter cables 122 and 124. Cavities 111a and 111b extend from top surface 112 to bottom surface 113. Hardenable material 89 is injected into implant 110 through injection cannula 118 (not shown). Biologics material 87 is injected into cavities 111a and 111b through biologics ports 116a and 116b, respectively (not shown). Injection cannula 118 is removable from implant 110 after hardenable material 89 has hardened. Perimeter cables 122 and 124 increase the strength of implant 110, and are arranged around wall 104 at the top surface 112 and bottom surface 113, respectively. Perimeter cables 122 and 124 further allow for radiologic assessment. Filaments 120 and 121 are intervening struts which cross implant 110 and add stability to the hardened construct. Filaments 120 and 121 further limit expansion once taut and serve to add tensile strength to the final construct similar to that of rebar in cement.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
30 Endoscope
31 Light guide connector
32 Light guide tube
33 Control body
34 Insertion tube
40 Surgeon
41 Monitor
45 Patient
48 Injector
50 Distractor
52 Means of attachment
54 Disc Space
56 Injection tube
57 Injection tube
58 Upper spacer
59 Lower spacer
60 Implant
66 Biologics port
68 Injection cannula
70 Implant (inflatable cage)
71 Cavity
72 Top surface
73 Bottom surface
74 Wall
76 Biologics port
78 Injection cannula
80 Implant (two-compartment inflatable cage)
80a First portion
80b Second portion
81 Cavity
82a Top surface
82b Top surface
83a Bottom surface
83b Bottom surface
84a Wall
84b Wall
85a Male connector
85b Female connector
86 Biologics port
87 Biologics material
88a Injection cannula
88b Injection cannula
89 Hardenable material
90 Implant (non-toroidal inflatable cage)
91a Cavity
91b Cavity
92 Top surface
93 Bottom surface
94 Wall
96a Biologics port
96b Biologics port
98 Injection cannula
100 Implant (inflatable cage with surface studs)
101a Cavity
101b Cavity
102 Top surface
103 Bottom surface
104 Wall
105 Studs
106a Biologics port
106b Biologics port
108 Injection cannula
110 Implant (inflatable cage with cable and filament enhancement)
111a Cavity
111b Cavity
112 Top surface
113 Bottom surface
114 Wall
116a Biologics port
116b Biologics port
118 Injection cannula
120 Filament
121 Filament
122 Perimeter cable
124 Perimeter cable

What is claimed is:

1. An endoscopically implantable inflatable interbody fusion device, comprising:
an inflatable body having an inner wall, an outer wall, a top surface, and a bottom surface;
a first cavity defined by the inner wall;
at least one hollow space between the inner wall and the outer wall;
a first delivery tube extending from outside the outer wall into the at least one hollow space; and,
a second delivery tube extending from outside the outer wall, through the at least one hollow space, and terminating in the first cavity; and,
at least one filament having a first end and a second end, the at least one filament is arranged in the at least one hollow space and the first and second ends extend from the outer wall;
wherein at least one of the inner wall, the outer wall, the top surface, and the bottom surface comprises an elastomeric material.

2. The inflatable interbody fusion device as recited in claim 1, wherein the first cavity extends from the top surface to the bottom surface.

3. The inflatable interbody fusion device as recited in claim 2, wherein the inner wall and the outer wall are perpendicular to the top and bottom surfaces.

4. The inflatable interbody fusion device as recited in claim 2, wherein the top surface and the bottom surface each comprise a plurality of studs.

5. The inflatable interbody fusion device as recited in claim 2, wherein the inner wall, the outer wall, the top surface, and the bottom surface are elastomeric.

6. The inflatable interbody fusion device as recited in claim 2, wherein at least one of the inner wall, the outer wall, the top surface, and the bottom surface are non-elastomeric.

7. The inflatable interbody fusion device as recited in claim 1, wherein the first delivery tube is removably connected to the outer wall.

8. The inflatable interbody fusion device as recited in claim 1, further comprising at least one perimeter cable arranged on the outer wall.

9. The inflatable interbody fusion device as recited in claim 8, wherein the at least one perimeter cable comprises a non-elastomeric material.

10. The inflatable interbody fusion device as recited in claim 1, wherein the at least one filament is non-elastomeric.

11. The inflatable interbody fusion device as recited in claim 1, wherein:
the inner wall comprises a first inner wall and a second inner wall;
the first cavity is defined by the first inner wall and a second cavity is defined by the second inner wall; and,
a third delivery tube extends from outside the outer wall, through the at least one hollow space, and terminates in the second cavity.

12. The inflatable interbody fusion device as recited in claim 1, wherein the inflatable body comprises:
a first section forming a first part of the inner wall, a first part of the outer wall, and a first hollow space of the at least one hollow space; and,
a second section removably connected to the first section, the second section forming a second part of the inner wall, a second part of the outer wall, and a second hollow space of the at least one hollow space;
wherein:
the first cavity is defined by the first part of the inner wall and the second part of the inner wall;
the outer wall is defined by the first part of the outer wall and the second part of the outer wall;
the first delivery tube extends into the first hollow space; and,
a third delivery tube extends from outside the outer wall into the second hollow space.

13. An endoscopically implantable inflatable interbody fusion device, comprising:
an inflatable body, including:
a top surface;
a bottom surface;
a first inner wall;
a second inner wall; and,
an outer wall;
a first cavity defined by the first inner wall;
a second cavity defined by the second inner wall;
at least one hollow space between the first and second inner walls and the outer wall;
at least one filament having a first end and a second end, the at least one filament is arranged in the at least one hollow space and the first and second ends are connected to the outer wall;
a first delivery tube extending from outside the outer wall into the at least one hollow space;
a second delivery tube extending from outside the outer wall, through the at least one hollow space, and terminating in the first cavity; and,
a third delivery tube extending from outside the outer wall, through the at least one hollow space, and terminating in the second cavity.

14. The inflatable interbody fusion device as recited in claim 13, wherein the inflatable body further comprises a top surface and a bottom surface and the first and second cavities extend from the top surface to the bottom surface.

15. The inflatable interbody fusion device as recited in claim 14, wherein the first inner wall, the second inner wall, and the outer wall are perpendicular to the top and bottom surfaces.

16. The inflatable interbody fusion device as recited in claim 14, wherein the top surface and the bottom surface each comprise a plurality of studs.

17. The inflatable interbody fusion device as recited in claim 14, wherein the first inner wall, the second inner wall, the outer wall, the top surface, and the bottom surface are elastomeric.

18. The inflatable interbody fusion device as recited in claim 14, wherein the first inner wall, the second inner wall, the outer wall, the top surface, and the bottom surface are non-elastomeric.

19. The inflatable interbody fusion device as recited in claim 14, wherein at least one of the first inner wall, the second inner wall, the outer wall, the top surface, and the bottom surface comprises an elastomeric material.

20. The inflatable interbody fusion device as recited in claim 13, wherein the first delivery tube is removably connected to the outer wall.

21. The inflatable interbody fusion device as recited in claim 13, further comprising at least one non-elastomeric perimeter cable arranged on the outer wall.

22. The inflatable interbody fusion device as recited in claim 13, wherein the at least one filament is non-elastomeric.

* * * * *